(12) United States Patent
Steinthal et al.

(10) Patent No.: US 7,171,312 B2
(45) Date of Patent: Jan. 30, 2007

(54) CHEMICAL AND BIOLOGICAL AGENT SENSOR ARRAY DETECTORS

(75) Inventors: Gregory Steinthal, Los Angeles, CA (US); Steven Sunshine, Pasadena, CA (US); Tim Burch, San Gabriel, CA (US); Neil Plotkin, Pasadena, CA (US); Chang-Meng Hsiung, Irvine, CA (US)

(73) Assignee: Smiths Detection, Inc., Pasadena, CA (US)

( * ) Notice: Subject to any disclaimer, the term of this patent is extended or adjusted under 35 U.S.C. 154(b) by 0 days.

(21) Appl. No.: 10/698,042

(22) Filed: Oct. 29, 2003

(65) Prior Publication Data
US 2004/0204915 A1 Oct. 14, 2004

Related U.S. Application Data

(63) Continuation-in-part of application No. 10/624,194, filed on Jul. 21, 2003, now Pat. No. 7,034,677.

(60) Provisional application No. 60/397,135, filed on Jul. 19, 2002, provisional application No. 60/422,301, filed on Oct. 29, 2002.

(51) Int. Cl.
*G01N 31/00* (2006.01)
*B32B 5/02* (2006.01)

(52) U.S. Cl. ................. 702/32; 422/82.02

(58) Field of Classification Search .......... 702/32, 702/22, 19; 73/31.05; 422/82.02; 340/522, 340/573.1, 511
See application file for complete search history.

(56) References Cited

U.S. PATENT DOCUMENTS

| | | | | |
|---|---|---|---|---|
| 4,846,166 A | * | 7/1989 | Willeke | 128/200.24 |
| 5,832,410 A | * | 11/1998 | Lin et al. | 702/22 |
| 5,833,603 A | * | 11/1998 | Kovacs et al. | 600/317 |
| 5,963,369 A | * | 10/1999 | Steinthal et al. | 359/410 |
| 6,017,440 A | * | 1/2000 | Lewis et al. | 205/777.5 |
| 6,117,643 A | * | 9/2000 | Simpson et al. | 435/7.1 |
| 6,198,394 B1 | * | 3/2001 | Jacobsen et al. | 340/573.1 |
| 6,199,550 B1 | * | 3/2001 | Wiesmann et al. | 128/204.23 |
| 6,330,464 B1 | * | 12/2001 | Colvin et al. | 600/316 |

(Continued)

OTHER PUBLICATIONS

Ziegler et al., Bioelectronic Noses: A Status Report. Part II, 1998, Biosensors & Bioelectronics 13, pp. 539-571.*

(Continued)

*Primary Examiner*—Michael Nghiem
*Assistant Examiner*—Toan M. Le
(74) *Attorney, Agent, or Firm*—Foley & Lardner LLP

(57) ABSTRACT

Chemical and biological detector systems, devices and apparatus. Such devices may be portable and wearable, such as badges, that are analyte-general, rather than analyte-specific, and which provide an optimal way to notify and protect personnel against known and unknown airborne chemical and biological hazards. The devices of the present invention are advantageously low-cost, have low-power requirements, may be wearable and are designed to detect and alarm to a general chemical and biological threat. A sensor device of the present invention in one embodiment includes two or more sensor devices, a processing module coupled to each of the sensor devices and configured to process signals received from each of the two or more sensor devices to determine an environmental state; and a communication module that communicates information about the environmental state to a user.

27 Claims, 22 Drawing Sheets

U.S. PATENT DOCUMENTS

| | | |
|---|---|---|
| 6,350,369 B1 * | 2/2002 | Lewis et al. ............. 205/777.5 |
| 6,422,061 B1 | 7/2002 | Sunshine et al. |
| 6,539,311 B1 * | 3/2003 | Berger ........................ 702/23 |
| 6,560,471 B1 | 5/2003 | Heller et al. |
| 6,606,567 B1 * | 8/2003 | Grate et al. ................... 702/22 |
| 6,627,154 B1 * | 9/2003 | Goodman et al. ....... 422/82.01 |
| 6,700,484 B1 * | 3/2004 | Bartholomew et al. ..... 340/531 |
| 6,711,423 B1 * | 3/2004 | Colvin, Jr. .................. 600/317 |
| 6,759,010 B1 * | 7/2004 | Lewis et al. ............. 422/82.02 |
| 6,773,926 B1 * | 8/2004 | Freund et al. .............. 436/149 |
| 6,823,717 B1 * | 11/2004 | Porter et al. ............... 73/31.05 |
| 6,826,117 B1 * | 11/2004 | Haase et al. ................ 367/119 |
| 6,854,317 B1 * | 2/2005 | Porter et al. ............... 73/31.05 |
| 6,867,048 B1 * | 3/2005 | Kovacs ....................... 436/149 |
| 6,868,350 B1 * | 3/2005 | Zimmermann et al. ....... 702/65 |
| 6,898,559 B1 * | 5/2005 | Saitta ............................ 703/1 |
| 7,034,677 B1 * | 4/2006 | Steinthal et al. ....... 340/539.12 |
| 7,045,097 B1 * | 5/2006 | Kovacs .................... 422/82.08 |
| 2002/0141901 A1 | 10/2002 | Lewis et al. |
| 2004/0029109 A1 * | 2/2004 | Lai ............................... 435/5 |

OTHER PUBLICATIONS

Porter et al., Sensor Based on Piezoresistive Microcantilever Technology, 2001, Sensors and Actuators A 88, pp. 47-51.*

McKennoch et al., Electronic Interface Modules for Solid-State Chemical Sensors, 2002 IEEE, pp. 344-349.*

Zee et al., MEMS Chemical Gas Sensor Using a Polymer-Based Array, Jun. 7-10, 1999, The 10th International Conference on Solid-State Sensors and Actuators.*

* cited by examiner

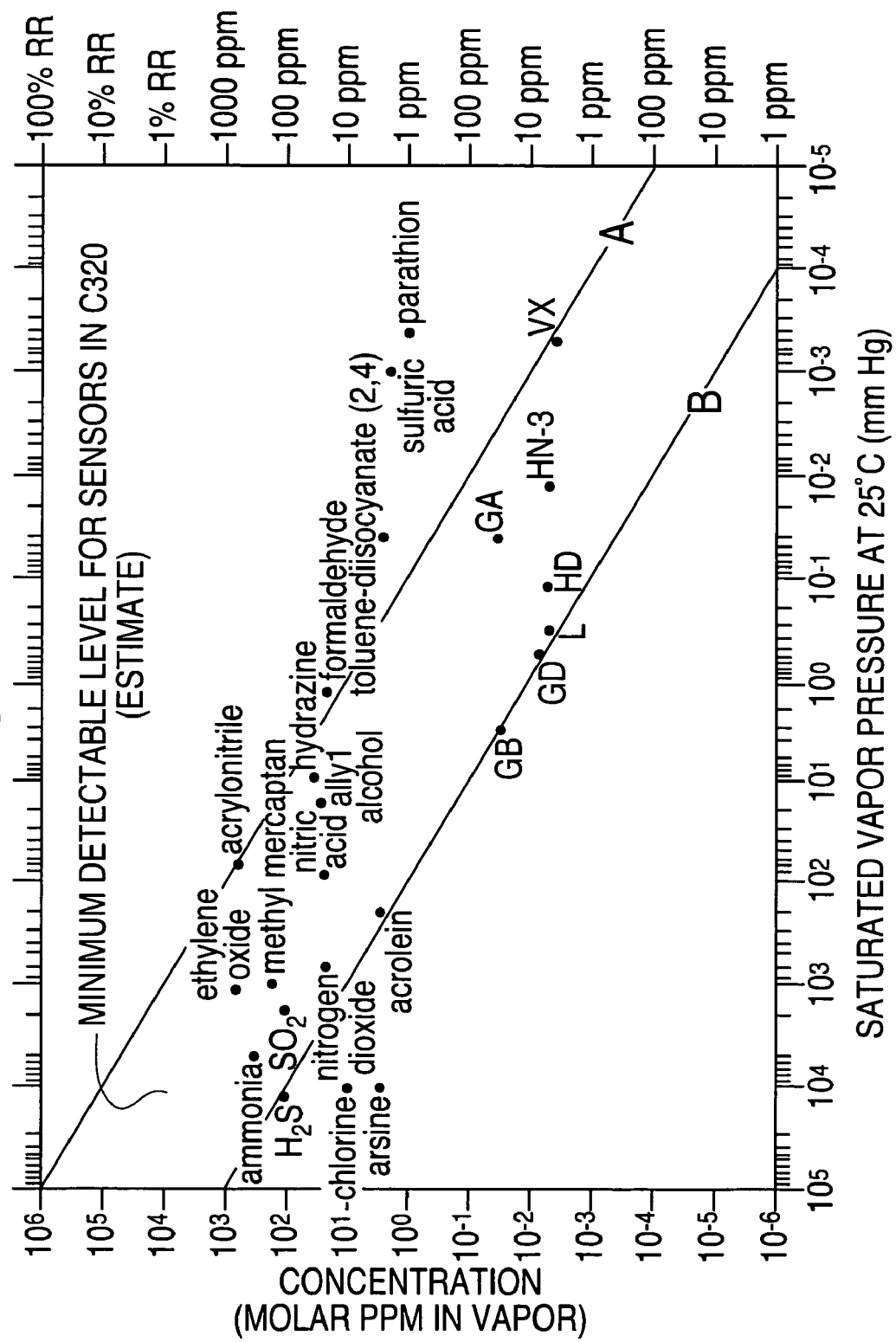

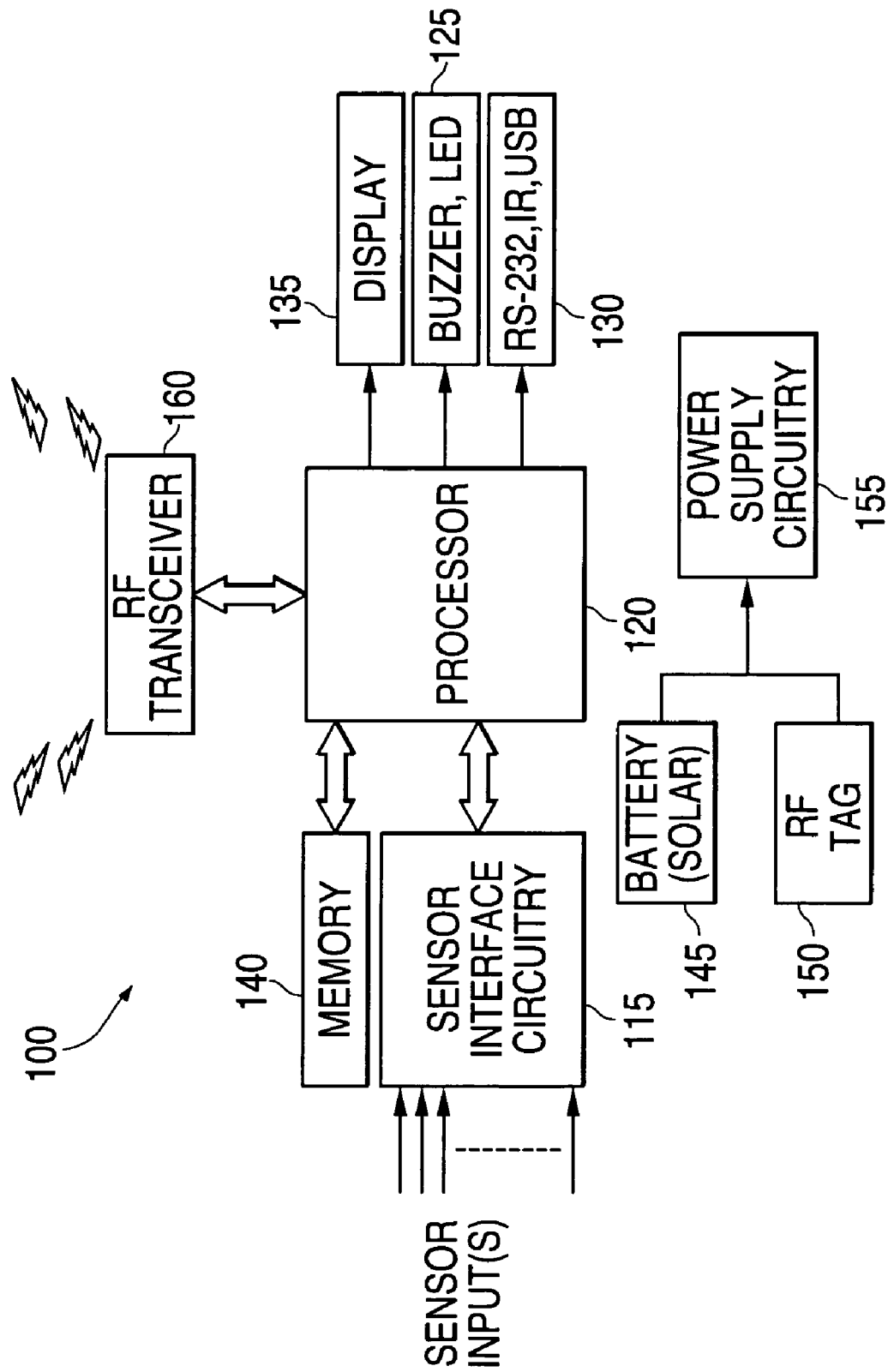

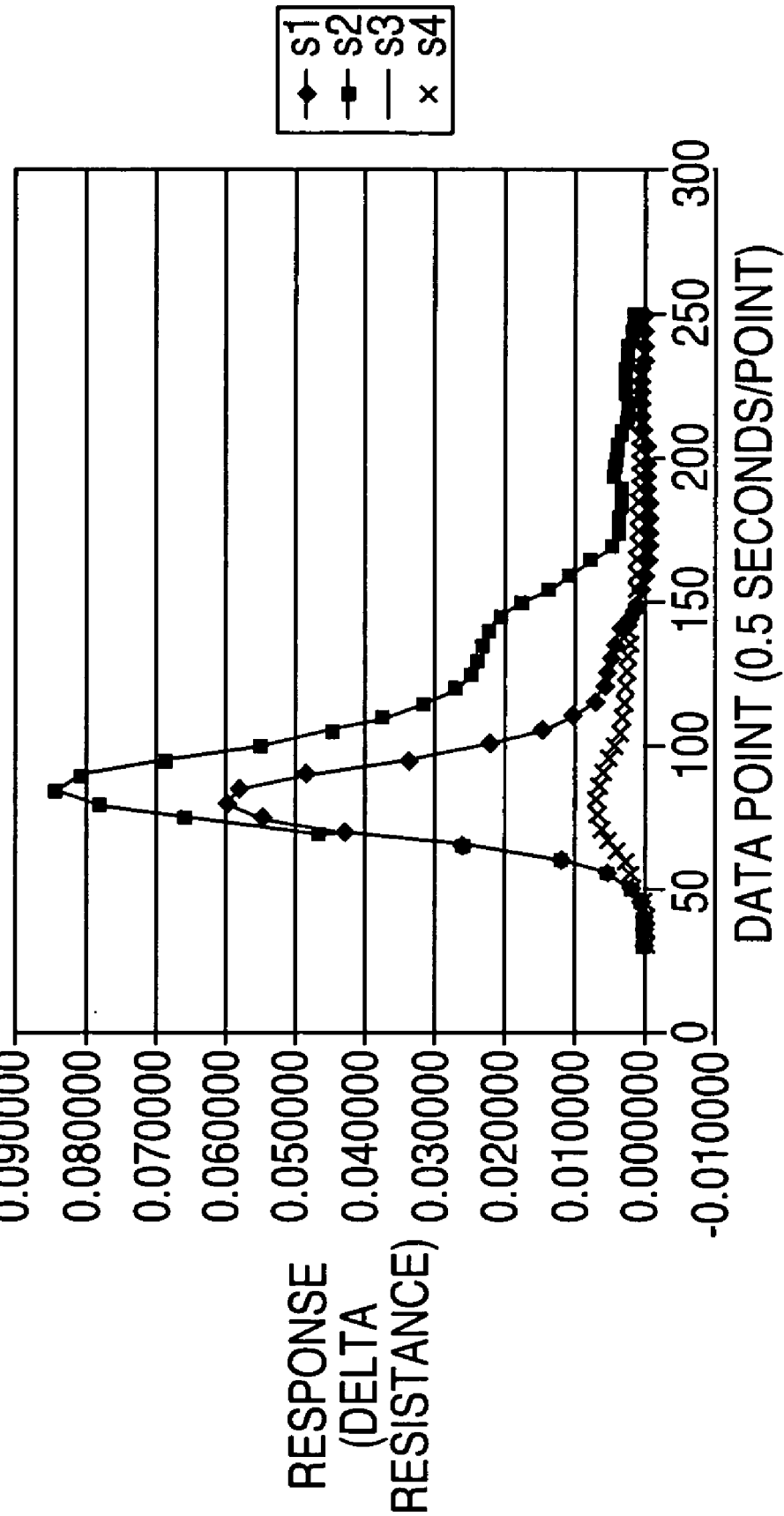

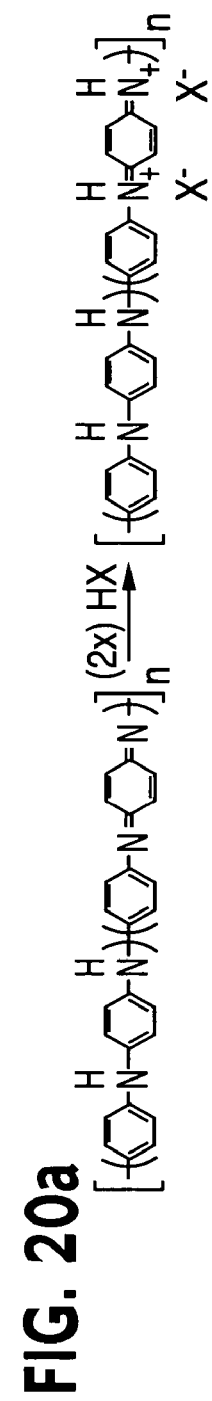
FIG. 19
FIG. 20a
FIG. 20b
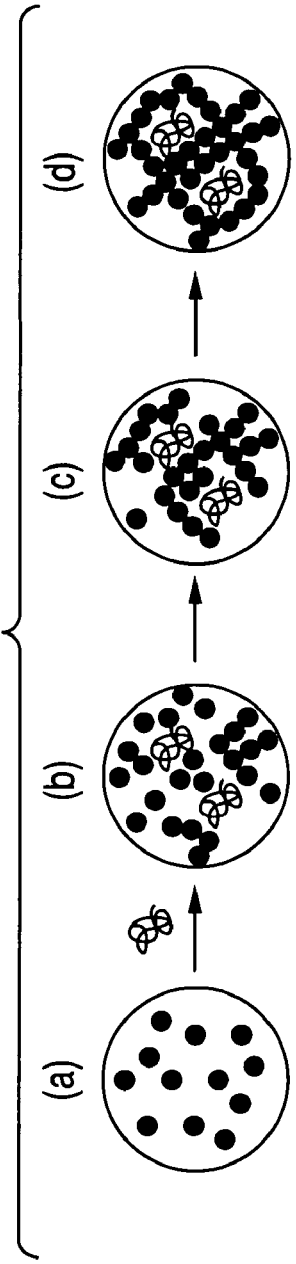
FIG. 21

CHEMICAL AND BIOLOGICAL AGENT SENSOR ARRAY DETECTORS

CROSS-REFERENCES TO RELATED APPLICATIONS

This application is a continuation-in-part application of U.S. patent application Ser. No. 10/624,194, filed Jul. 21, 2003 now U.S. Pat. No. 7,034,677, which is a non-provisional of, and claims benefit of, U.S. Provisional Application Ser. No. 60/397,135, filed Jul. 19, 2002, both entitled "Non-Specific Sensor Array Detector Badges", both of which are hereby incorporated by reference in their entirety for all purposes. This application also claims the benefit of U.S. Provisional Application Ser. No. 60/422,301, filed Oct. 29, 2002, entitled "Nanomaterial-Based Large Scale Resistive Arrays", which is hereby incorporated by reference in its entirety for all purposes.

STATEMENT AS TO RIGHTS TO INVENTIONS MADE UNDER FEDERALLY SPONSORED RESEARCH OR DEVELOPMENT

NOT APPLICABLE

BACKGROUND OF THE INVENTION

The present invention relates to detector systems for chemical and biological sensing. The present invention also relates to small form factor, portable, handheld and wearable detector systems and in particular to portable, handheld and wearable detector systems including sensor arrays configured for biological and chemical analyte detection, and which are configurable with software modules to detect and analyze a variety of environmental conditions and which have low operating power requirements and long lifetimes.

Civilian and military personnel, Coast Guard and Customs, State and Federal Emergency Responders, and Industrial Workers would greatly benefit from a personal early-warning system to identify changes in environmental conditions, such as the release of hazardous airborne chemicals or biological agents, in time to either evacuate or don protective equipment, such as chemical protective equipment (CPE). For example, releases of toxic industrial chemicals (TICs) may occur accidentally in the course of normal operations, from unseen leaks in fueling, heating or cooling systems, or from intentional hostile actions. Additionally, chemical warfare agents (CWAs) and biological warfare agents (BWAs) may be released during combat or in other potentially hostile situations such as during terrorist activity. Each of these situations presents a unique and potentially broad range of chemical and biological threats that typically cannot be identified a priori. There is a need to detect and characterize TICs, CWAs, BWAs and other environmental conditions before hostile exposure in order to take appropriate actions to neutralize the threat. A similar need exists after a TIC, CWA or BWA release to identify the chemical or biological agent class such that appropriate defensive and decontamination measures may be taken.

While laboratory instruments with high specificity and accuracy are available, they are not generally suitable for field use because they lack physical robustness, require highly trained operators, and typically are not portable due to size, weight, high power consumption requirements, and chemical reagent (gases, liquids) requirements. In addition, specialized portable instruments for one threat type, (e.g. CWA) may not work for the other threat types of interest, (e.g. explosives, fire, BWAs or TICs) or for improvised devices.

Handheld as well as wearable, passive detectors for hazardous conditions such as TICs, BWAs and CWAs will greatly improve the safety of the personnel operating in threatened environments. Useful known portable detectors include point detectors and standoff detectors. One chemical point detector, the Joint Chemical Agent Detector (JCAD), is hand held and portable but has a limited operational life on a single charge, requiring frequent recharging. In addition, the JCAD has to be handled impairing use of other devices simultaneously. Standoff detectors, such as the Joint Services Lightweight Standoff Chemical Agent Detector (JSLSCAD), can continuously protect personnel from CWAs, but (1) lack spatial resolution and (2) have detection limits much larger than the Immediately Dangerous to Health and Life (IDLH) level. General limitations of current badge or wearable detectors (e.g., SafeAir, ToxiRAE) include: 1) analyte-specificity: these require detailed a priori knowledge of chemical hazards, or multiple badges for broad spectrum coverage, and cannot detect new or unknown hazards; 2) single-use: disposable detectors and dosimeters require re-supply for continuous protection; 3) interpretation errors: colorimetric indicators require visual comparisons (color cards) that are prone to user subjectivity; 4) no alarm modes or communications capability: these do not provide rapid hands-free warning or transmission of status; 5) environmental performance: extremes of temperature (e.g., <0° or >40° C.) and humidity (e.g., <10% or >90% relative humidity (RH)) limit some sensors (e.g., electrochemical, conducting polymers). Such detectors also do not typically include datalogging capability (e.g., storing detailed historical information/records of the environment encountered), or may only provide a time-averaged history of exposure. Additionally, current detectors also typically have high operational power requirements and, therefore, typically short operational lifetimes. For example, the JCAD requires recharging or replacement of the power supply every 20 hours or less.

Some sensor devices, such as the ToxiRae Plus, produce audible and vibratory alarms, eliminate interpretation errors, and have datalogging capability, but these wearable sensors are still analyte-specific. In addition, these sensors are not useful as badge detectors since they require a pocket or belt clip due to their size and weight.

Wearable sensor devices with analyte-general capability have been developed, e.g., by EIC Laboratories, Inc. and Physical Sciences, Inc., however these devices have significant performance issues with humidity that are likely to affect the ruggedness and stability of the sensors during field-use of the badge detector.

While improvements have been made in the field of chemical and biological sensing, the diverse set of potential target compounds and numerous sensing methodologies has limited progress. Most current low-cost sensors are based on a single sensing approach optimized to detect one, or a class, of compounds.

On the biological side, significant recent research has been directed toward fluorescence-based arrays for genomic and proteomics applications (Kristensen et al., *Biotechniques*, 30(2):318 (2001); Harrinton, et al., *Curr. Opin. Microbiol*, 3(3):285 (2000); Katsuma et al., *Expert Rev. Mol. Diagn.*, 1(4): 377 (2001); Templin et al., *Trends Biotechnol*, 20(4):160 (2002); Schweitzer et al., *Curr. Opin. Biotechnol*, 13(1):14 (2002); Gabig et al., *Acta Biochim. Pol.*, 48(3):615 (2001); Weinstein et al., *Cytometry*, 47(1):46 (2002)). These arrays all focus on a single sensing approach, most often related to binding of a fluorescent probe. Because of the complex nature of reading and interpreting these arrays, they are always associated with laboratory based analytical instruments and are not compatible with widely distributed sensing networks.

While high density sensor arrays have recently been developed for biological detection, these sensors often require a significant amount of wet chemistry prior to detection and are based on relatively complicated and expensive read out electronics such as optical readers. Furthermore, since these arrays rely exclusively on specific binding, these arrays are not effective chemical sensors and require a great deal of customization of each sensor element.

There is therefore a need for improved sensors and detector systems for biological and chemical sensing. There is also a need for personal detector systems (e.g., portable and wearable detectors) that overcome the limitations of current detectors and which provide personnel with continuous, reliable protection in a potentially dangerous environment. The present invention satisfies these and other needs.

BRIEF SUMMARY OF THE INVENTION

The present invention provides improved biological and chemical analyte detection systems and devices. The present invention also provides portable and wearable detector systems and devices, such as badges. In certain aspects, such systems and devices are analyte-general, rather than analyte-specific, and therefore provide an optimal way to notify and protect personnel against known and unknown environmental conditions and events such as airborne chemical and biological hazards, without the device having to be handled. Such devices according to aspects of the present invention are advantageously low-cost, have low-power requirements, may be wearable and are designed to detect and alarm to a general environmental threat.

Devices according to one aspect of the present invention include software modules configured to analyze sensor signals to provide for detection and identification of a variety of environmental conditions such as, for example, a release of TICs, BWAs and CWAs. Such devices therefore advantageously allow for protecting more individuals at lower cost and without specialized training than expensive point detectors, stand-off area monitors, or existing detector badges that are limited to single chemical detection. According to another aspect, devices of the present invention include communication modules and are implemented in a network, such as a distributed network of sensor devices.

As used herein, an environmental event, condition or state may include, for example, an environmental parameter such as temperature, humidity or pressure, radiation level, or other physical stimuli, the presence or a level of an atmospheric constituent such as an airborn chemical or vapor, the presence or a level of a liquid or fluid constituent such as a chemical, a biological agent or material, a therapeutic agent, and others. A change in an environmental state or condition may include an increase or a decrease in the level or presence of an environmental parameter.

In certain aspects, detector devices of the present invention include one or more of the following features or attributes:

uses a non-specific sensor array to detect one or multiple environmental conditions, e.g., TICs and CWAs at IDLH levels,
uses polymer-composite sensors which are stable in the presence of moisture,
measures relative humidity and ambient temperature,
can be used in a wide range of operating conditions (relative humidity: 0–99% non-condensing; temperature: −15° C. to 40° C. or greater)
is passive and requires no user-interaction or user-attention during field-use,
includes downloadable flash memory to maintain an historical data record,
provides an audible alarm and inaudible alarm when TIC, BWA or CWA is detected,
includes an audible and inaudible periodic signal during normal operation,
is smaller than a credit card and weighs ounces,
has a battery lifetime of at least two weeks or more (e.g., multiple years) during continuous field-use,
has at least a two-year shelf-life,
meets the requirements for high-volume manufacturing,
has a low cost of goods and services (e.g., approximately $30 rough order of magnitude) for large volumes,
can be directly integrated into existing products (e.g., wireless sensor networks for detecting industrial chemical leaks and the release of CWAs in public facilities) to increase the available market size.

According to certain aspects of the present invention, polymer-composite sensor technology is used to construct arrays of two or more sensors useful for various applications, such as portable or wearable detector devices for detecting and analyzing environmental conditions and changes therein such as the presence of TICs, BWAs and CWAs. Such devices including PCS sensors are particularly advantageous as they can be configured to be compact, light-weight, wearable, rugged, stable, low-cost, low-power, and analyte-general. Polymer-composite sensors do not have the same humidity-performance limitations as conductive-polymer sensors. Since polymer-composite sensors are low-power sensors rather than no-power sensors (e.g., current off-the-shelf (COTS) badge detectors), detector devices according to certain aspects of the present invention are able to produce alarms with no interpretation errors and allow for datalogging capabilities. By combining a sensor array with techniques for detection and identification, detector devices according to certain aspects of the present invention are advantageously non-analyte-specific, addressing another limitation of current COTS detectors and others.

According to an aspect of the present invention, a biological agent detection apparatus is provided. The apparatus typically includes a substrate, and an array of two or more sensors arranged on the substrate, wherein at least a first one of the sensors includes a sensing element configured to detect a biological agent. The apparatus also typically includes a processing module, directly coupled to each of the sensors, configured to process signals received from the two or more sensors to produce an output signal.

According to another aspect of the present invention, a sensor system is provided. The system typically includes a plurality of sensing devices, each device including an array of two or more sensors arranged on a substrate and a wireless communication module for remote communication. The system also typically includes a central processing node, located remote from said sensing devices, including a processing module and a communication module, said node being configured to receive and process signals from the plurality of sensing devices.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

BRIEF DESCRIPTION OF THE DRAWINGS

FIG. 2 is a chart which illustrates IDLH levels of various agents. In this chart, the points denote concentrations of Immediately Dangerous to Life and Health (IDLH) levels. Chemical warfare agents and toxic industrial chemicals are shown. Chemicals with points above the region for the minimum detectable level have a high probablity of being detected at IDLH levels by the sensor array in a sensor arrangement such as a Cyranose™ 320 (C320), for example. Chemicals having points within the region have a moderate probability of being detected at IDLH levels, while chemicals having points below the region have a low probability of being detected at IDLH levels FIGS. 3a and 3b illustrate portable detection devices according to embodiments of the present invention.

FIG. 4 shows a typical response curve to a transient event. In this case the response curve depics, merely by way of example, a four-channel chemical-event detector being exposed to a transient chemical response.

FIG. 19 shows a table of four SMCB materials.

FIGS. 20a and 20b show the chemical structures of polyanilinapolyaniline and polythiophene, respectively. FIG. 20a depicts the chemical structure of polyaniline in its insulating state and its conducting state following protonation by an acid HX, while FIG. 20b shows the chemical structure of poly(3-subsituted-thiophene) wherein R=H, or alkyl, and wherein [OX]=oxidizing agent, in its insulating state and its conductive state (following oxidative "doping").

FIG. 21 illustrates a sol-gel encapsulation process as a schematic diagram of a sol-gel encapsulation of indicator biomolecules, wherein (a) shows the formation of sol particles during initial hydrolysis and polycondensation; (b) shows the addition of indicator biomolecules to the sol; (c) shows the growing silicate network beginning the trap the biomolecules; and (d) shows the indicator biomolecules immobilized in the gel.

DETAILED DESCRIPTION OF THE INVENTION

Figure 1A:
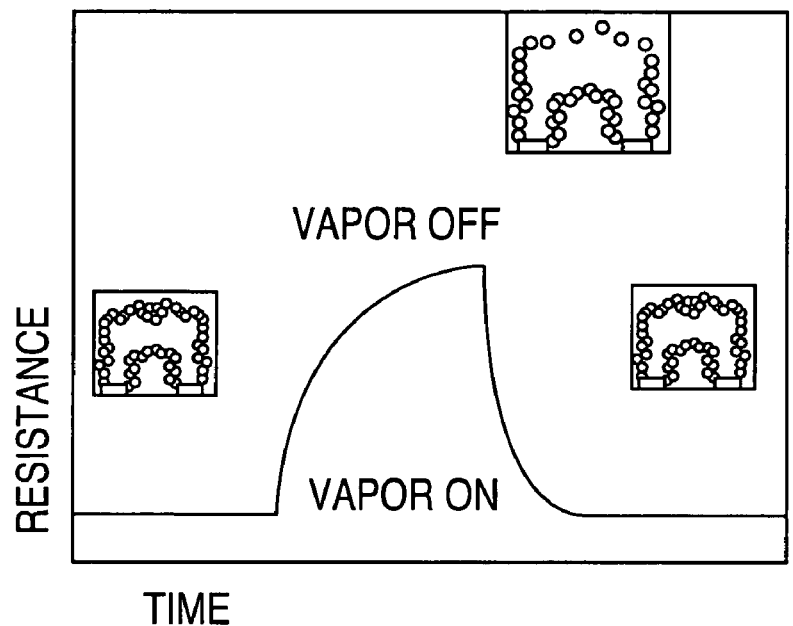
FIGS. 1a and b illustrate a representation of a composite detector material responding during an analyte exposure, and a representation of how data are converted into response patterns, respectively according to an aspect of the present invention.

The present invention relates to an integrated resistance-based chemical and biological sensing system on a silicon chip. Such chips according to the present invention are advantageously low-cost, low power, small, rapidly responding devices that can detect, classify, quantify, and track a wide variety of chemical and/or biological species in air or other carrier medium. Such devices are able to detect these species at concentrations of up to three orders of magnitude lower than current low-cost sensor technology. These chips are also advantageously consistent with distributed networks, such as low-cost (<$5 per node), self-assembling, wireless networks, such that chemical and biological sensing may become as ubiquitous as temperature and pressure sensing. Such devices result in enhanced safety, improved manufacturing, and a cleaner environment.

The present invention exploits a number of chemical and biological sensing technologies that are VLSI compatible and which have a number of superior chemical sensing performance properties relative to most previously available systems. Sensing materials include nanoparticle composite sensors such as polymer composite sensors, sensors based on nanotubes, and sol-gel based biological sensors (biogels). In addition, intrinsically conducting polymer sensors are also used. The present invention also provides fabrication techniques for the deposition of nanoliter size drops of these complex composite materials. The present invention also provides a number of solutions or suspensions of sensing materials that are stable dispersions at the nanometer size regime.

The present invention provides a broadly useful chemical and/or biological sensor that can be utilized across a wide range of applications and therefore drive volumes that may result in extremely low-cost sensing. Chemical and biological sensing is generally relegated to laboratories using highly sophisticated instruments or to point measurements using hand-held devices. No broad-based, low-cost, sensing technology exists that can be easily deployed across a wide range of applications (as a pH meter or gas chromatograph can be in the laboratory setting). Since each potential application has limited volumes, very low-cost devices do not exist, except, for example, carbon monoxide sensors which have been adopted on a much wider basis.

Applications for this low-cost solution are numerous and include, but are not limited to, fire protection, leak detection, filter bed monitoring and medical diagnosis. Each of these applications is characterized by a wide range of potential target compounds. A few examples are mentioned below but the overall economic impact goes well beyond those listed.

Detector devices according to the present invention preferably include an array (i.e., at least two) of polymer-composite sensors. A polymer-composite sensor (PCS) typically includes a conducting media, a polymeric phase, and two electrodes. When a voltage is applied across the electrodes, electrons travel across the sensor via pathways consisting mainly of the conducting media, and sensor resistance is measured. Sensor resistance is one of the simplest measurements of the state of the sensor and is related to the number of molecules sorbed in the sensor—a change in sensor resistance is proportional to a change in the mass of sorbed molecules. In certain aspects, The PCS sensors, or other sensors in an array of sensors, are modified as described herein to optimize chemical and/or biological analyte detection. For example, in one aspect, a specific receptor is grafted, or otherwise attached, to the surface of a conductive particle for specific biodetection applications. As another example, traditional electrodes are replaced with microfabricated vertical carbon nanotube electrodes in one aspect. The nanoscale size results in a small time constant and a low ohmic drop, thereby enhancing detector sensitivity.

In a PCS sensor, when there is a change in the chemical vapor that is in contact with a sensor, there is a concomitant response such as a change in sensor resistance. A change in the vapor phase causes a change in the chemical potential of its components and a subsequent difference in chemical potential between the sensor and the vapor phase. This difference in chemical potential results in a net transport of molecules into or out of the sensor, depending on whether the vapor or the sensor has greater chemical potential for that component. This net transport of molecules causes a change in the resistance since the number of sorbed molecules in the sensor changes, and the net transport continues until the chemical potential of all components is the same in the vapor and sensor. FIG. 1A shows a representative sensor response to a step change in the concentration of an analyte. For a period of time, the sensor is exposed to air and the sensor resistance, $R_{baseline}$, is constant since the stimulus is also constant. The sensor is then exposed to a vapor ("vapor on") that contains air and an analyte that wasn't present during the baseline, causing an increase in the chemical potential of the vapor phase. Molecules of analyte travel from the vapor phase into the sensor, causing an increase in the number of molecules that are sorbed in the sensor and an increase in sensor resistance, R. When the sensor is no longer exposed to the analyte ("vapor off") and is exposed only to air again, analyte molecules desorb from the sensor and the sensor resistance decreases to the baseline resistance. The sensor response is calculated by:

$$\Delta R = (R - R_{baseline})/R_{baseline}. \quad [1]$$

Figure 1B:
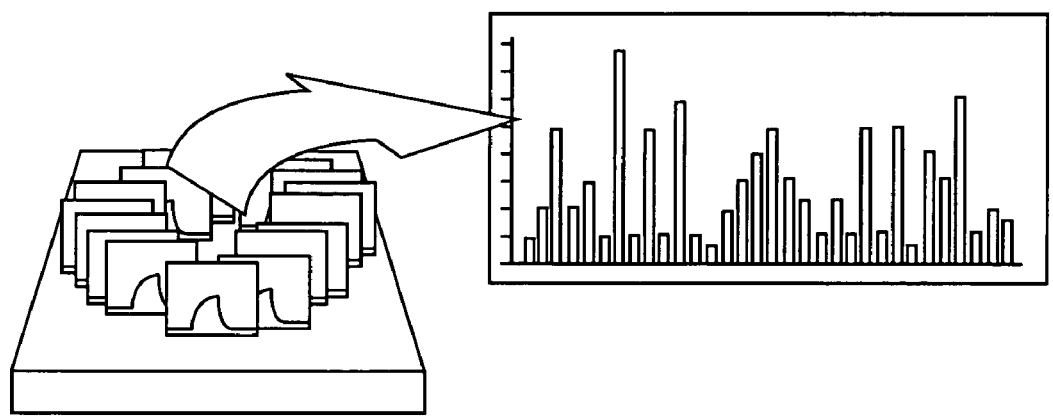

When a vapor is presented to an array of polymer-composite sensors, the array produces a pattern, as shown in FIG. 1B, since most, if not all, sensors in the array preferably produce different responses. The chemical potential of a vapor component is proportional to the percent saturated vapor pressure. (Percent saturated vapor pressure is equivalent to relative humidity for water content.) The chemical potential of a vapor component in the sensor is proportional to the number of sorbed molecules and is inversely proportional to the average interaction energy of the sorbed molecule with the sensor materials. A change in the sensor resistance is proportional to the change in the mass of sorbed molecules. At equilibrium, when the chemical potentials of each component in the vapor phase and the sensor are equal, the sensor response follows the scaling argument:

$$(\Delta R/R)_j \sim \sum_i \epsilon_{ij} \Delta [P_i / P_{sat,i}(T_{sensor})]_i, \quad [2]$$

where $(\Delta R/R)_j$ is the sensor response for the $j^{th}$ sensor in the array, $\epsilon_{ij}$ is the interaction energy between the $i^{th}$ component in the vapor and the $j^{th}$ sensor in the array, $P_i$ is the partial pressure of the $i^{th}$ component in the vapor, $P_{sat,i}$ is the saturated vapor pressure of the $i^{th}$ component in the vapor phase at the sensor temperature, $T_{sensor}$. Since the interaction energy, $\epsilon_{ij}$, is different for each analyte-sensor pair, the response of each sensor in the array will be different for the same vapor. The interaction energy, $\epsilon_{ij}$, is a measure of sensor sensitivity to a given analyte and in certain aspects has values ranging nearly two orders of magnitude for different analyte-sensor pairs. Although PCS sensors are preferred, it is understood that sensor devices according to the present invention may include other sensor types in addition to, or alternatively to, PCS sensors.

U.S. Pat. Nos. 5,571,401 and 5,788,833, each of which is hereby incorporated by reference in its entirety for all purposes, disclose chemical sensors useful for detecting analytes in a fluid (e.g., liquid, gas) as well as useful polymer-composite materials for polymer-composite sensor systems and devices. U.S. Pat. No. 6,537,498, which is hereby incorporated by reference in its entirety for all purposes, shows colloidal particles and other materials useful in the sensors devices of the present invention.

In one aspect, the present invention provides highly engineered sensors created from nanometer-sized carbon black particles stabilized with molecules or polymers attached directly to the carbon surface. These surface-modified carbon black (SMCB) sensor materials can be dispersed in a solvent and result in suspensions that preserve the nanometer-scale particles where typical carbon black/polymer dispersions aggregate at the micron size regime. These materials are highly suitable to the low-volume jetting processes of the present invention. In addition, the sensitivity of these materials is equal to or greater than similar composite sensors that do not utilize the surface modification approach. Extending this demonstrated capability to a range of chemically distinct sensing materials is advantageous.

Several other resistive-based sensing technologies are also compatible with the sensor deposition techniques of the present invention. One specific sensing technology is intrinsically conducting polymers. While intrinsically conducting polymer sensors have been known for some time, historically these materials have been susceptible to moisture resulting in unreliable sensor performance. Recently, new materials have been fabricated for display purposes that show much greater stability to moisture. Traditionally, these intrinsically conducting materials have high sensitivity for certain high vapor pressure compounds including chlorine-, ammonia-, and sulfur-containing gases.

Another class of materials that is suitable for use in the present invention is carbon nanotubes. The chemical detection capabilities of these materials have been recently reported (Kong, et al., *Science*, 287(5453):622 (2000)). In these reports, these materials are manually manipulated to lie between parallel electrodes. Furthermore, manufacturing variability of single nanotubes is very high. By averaging behavior over a number of nanotubes, single tube variability can be reduced or eliminated. This will lead to a more reliable and economical manufacturing path than has been previously demonstrated. In certain aspects, the present invention provides methods to deposit nanotubes directly from a solvent that completely evaporates. This approach focuses on using one or multiple nanotubes in a, single sensor.

Another set of materials that is used in one aspect is surface-modified colloidal metal particle sensors other than carbon black. These include surface-modified gold nanoparticles as chemical sensors similar to the surface-modified carbon blacks described above. Use of these materials as biopolymer based sensors has been demonstrated (Frey et al., *Langmuir*, 17(8):2408 (2001); Ostuni et al., *Langmuir*, 17(9):2828 (2001); Engelkamp, *Science*, 284(5415):785 (1999)). These materials are often referred to as self-assembling monolayer (SAM) sensors since alkane thiols are often used as the surface modifier which form a monolayer on the metal surface. In the present invention, both traditional polymer modified gold nanoparticles and biopolymer modified gold nanoparticles may be used as resistance based chemical and biological sensors. The resistive read out provides a more robust measurement compared to optical detection that requires the alignment of lightsource, surface, and detector that currently limits these devices to laboratory use. A second advantage is that these materials are compatible with the sensing and deposition methodologies of the present invention. These materials have been demonstrated as effective sensors. The fabrication of these sensors is generally similar to that of the carbon-black-based systems.

In addition to the surface-modified biopolymer sensor mentioned above, there is a second emerging biodetection technology useful in the present invention. The technology, developed at HRL (formerly Hughes Research Laboratory), involves sol-gel encapsulated enzyme-based sensors. These biosensors are based on conductive polymer transducers coupled with bioindicator molecules (e.g., enzymes) which are encapsulated within sol-gel matrices (biogels). These sensor elements detect analytes in water, and air (including aerosols) and detect analytes in soil, as well. Detection is accomplished by monitoring the change in resistance of the conductive polymer. The power consumption is extremely low (on the order of microwatts) so battery life is long. This sensor approach has been utilized to detect sporylated bacteria from an aerosol at the 1000 organism level. A key advantage of this biosensor is that it can operate without consumables and can detect directly in air.

In certain preferred aspects, an array of multiple, e.g., 32 sensors, is implemented in the devices of the present invention, but arrays can be comprised of fewer sensors or even more sensors as desired for the particular application. For certain specific applications, an array of only four or five sensors is typically sufficient if sensors are appropriately selected. In preferred aspects, an array of sensors includes a single PCS sensor or multiple PCS sensors. Also, the array may include none, one or more other sensor types.

U.S. Pat. No. 6,085,576, which is hereby incorporated by reference in its entirety for all purposes, discusses aspects of an example of a handheld sensor system, which includes a relatively large number of sensors incorporated in a handheld device that is intended to be used for a wide range of applications. One such sensor, the Cyranose™ 320 (C320), is a COTS handheld vapor identification system that, in one aspect includes: (1) a polymer-composite sensor (PCS) array that returns a signature pattern for a given vapor, (2) a pneumatic system to present that vapor to the sensor array, and (3) implementations of pattern recognition algorithms to identify the vapor based on the array pattern. The C320 has been successfully tested as a point detector for TICs (e.g., hydrazine, ammonia, formaldehyde, ethylene oxide, insecticides) as well as CWAs (e.g., GA, GB, HN-3, VX).

Figure 3A:
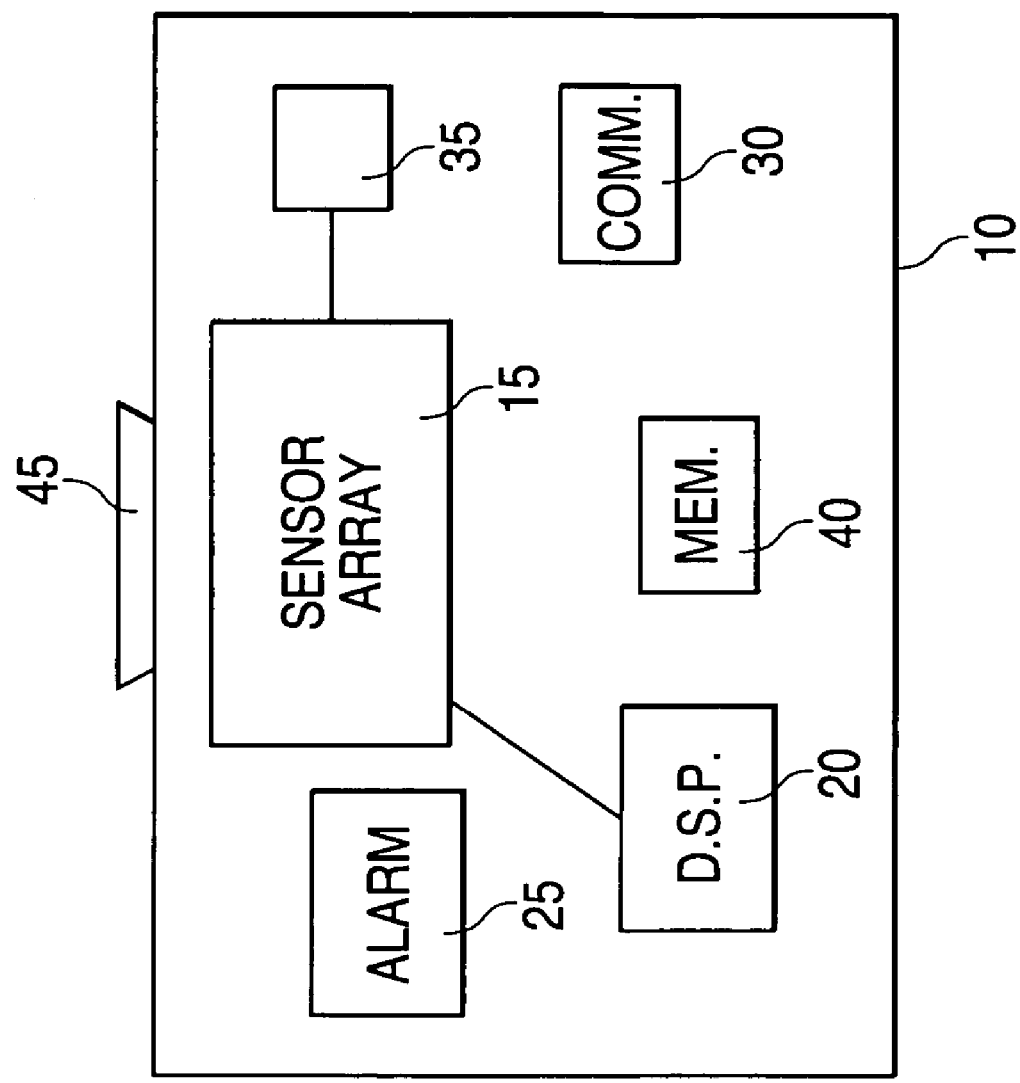

FIG. 3a illustrates a portable detector device 10 according to an embodiment of the present invention. It is preferred that the housing structure is small. Device 10 includes an array 15 of one or more sensors, preferably one or more polymer-composite sensors (PCS) as discussed herein. Digital signal processing (DSP) unit 20 receives and processes signals from sensor array 15 and stores data to memory 40. Pneumatic pump system 35 is optionally provided to assist with providing vapor to sensor array 15. In certain aspects, alarm module 25 is included to provide an active alarm when an alarm condition has been determined, e.g., when a programmable or preset threshold condition or value is exceeded. Alarm 25 can include a light such as an LED, a vibration module and a sound emitting module, e.g., including a speaker. One or more communication modules 30 are provided for interfacing with external intelligence such as a central alarm system. In one aspect, a communication module 30 includes an interface device such as an RF transmitter (or transceiver) for transmitting RF signals to an external device such as a command system or relay node. Communication module 30 can also include a receiving device such as an RF antenna (or transceiver) for receiving commands and data. Other useful interface types include IR transmitters, Bluetooth, RS-232, USB and Firewire interfaces, and any other wireless and physical connector interfaces (and associated protocols) for interfacing with external intelligence devices and systems such as a computer system. U.S. Pat. No. 6,422,061, which is hereby incorporated by reference for all purposes, discloses handheld sensor systems configured to interface, e.g., wirelessly, with a distributed network.

All components of device 10 are preferably coupled via one or more busses, but they may be individually directly connected as suitable for particular applications. In wearable badge device embodiments, an attachment device 45 such as a clip, strap or a pin is provided for attachment to a pocket, shirt lapel, belt, around the neck, etc as is convenient or necessary for the particular application. A battery and battery status monitor (e.g., LED light) are also preferably included (but not shown).

FIG. 3b illustrates a portable detector device 100 according to another embodiment of the present invention. In preferred aspects, device 100 is portable, wearable, has low power requirements and is self-calibrating. As shown, device 100 includes sensor interface circuitry module 115, which is configured to receive signals from a sensor array (not shown) and provide signals to a processor module 120 (e.g., DSP). Processor module 120 processes the received signals as will be discussed herein to detect and identify various environmental events or conditions. Memory 140 is used by processor module 120 to store various data, parameters and algorithms associated with event detection and identification. RF transceiver module 160 is configured to transmit and receive information to and from an external intelligence source such as a remote computer system, a base station or node in a distributed network of sensors, a remote alarm system, etc. Alarm module 125 includes one or more of a visual indicator such as an LED, an auditory indicator such as a buzzer or speaker and a vibratory indicator. Processor 120 activates alarm module 125 in response to detection and/or identification of an alarm event. An optional display 135 is provided to allow a user to view information related to event detection and identification processing. Communication module 130 is included to provide a communication path to external intelligence, whether directly connected (e.g., USB, Firewire, RS-232) or remotely connected (e.g., wireless). It will be appreciated that one or both of modules 160 and 130 may be implemented on detector device 100.

Power supply circuitry module 155 is provided to control various modes of operation of device 10. As will be described in more detail below, for example, power supply control circuitry is configured in certain aspects to place device 100 in a sleep mode, or reduced power consumption mode, and to awaken device 100 and place it in a full power consumption mode. Battery 145 is provided as a power supply source. Battery 145 may include a conventional battery, a solar cell or other power source. Alternatively, or in addition to battery 145, RF Tag module 150 is provided in some embodiments to allow for remotely powering up device 100 as will be discussed in more detail below. An attachment device (not shown) is also included in wearable device embodiments.

Devices 10 and 100, in certain aspects, are preferably implemented in or on a housing structure such as a card-shaped or badge-shaped plastic structure, or other compact structure allowing for ease of use, transport, wearability, attachment to a user, etc. Additional aspects of sensor devices of the present invention, such as sensor devices 10 and 100, including portability and wearability, low power consumption, self-calibration, and event detection and identification will now be described with particular attention to implementations including polymer-composite sensor (PCS) elements. It is understood, however, that sensor elements other than PCS elements may be additionally or alternatively used.

Sensor Interfaces

Referring to polymer-composite sensor arrays, a constant current source is provided to deliver constant low level dc current independent of the load. Studies indicate a significant reduction in sensor noise with bias currents less than 100 uA. Sensors have been shown to operate with as little as 5–10 uA. Also constant current provides a more accurate means to detect sensor response due to a high degree of linearity.

Low Power Consumption

Typical polymer-composite sensor elements exhibit a base resistance of between about 2 KOhms and about 100 KOhms, nominally about 10 KOhms. The peak power consumption (per sensor element) can easily be calculated (using a 10 uA constant current driving scheme) as follows:

$$Ppk=(10E{-}6)*(10E{-}6)*(10E3)=10\ nW$$

Further this number can be reduced if the sensors do not need to be constantly active. That is the average power:

$$Pavg=Ppk*DF$$

where DF is the duty_factor representing the percentage of the conversion time/response time. Conversion times represent the total time it takes to capture the sensor response and process the information. The conversion times are typically on the orders of milliseconds.

In one aspect, operation of devices of the present invention advantageously require less than about a milliwatt of power, and even less for certain device embodiments including only PCS sensors. The typical lifetime of a device operating at 1 milliwatt is on the order of approximately several weeks to several years or more. Further, power management capabilities reduce the power requirement as well as increase the lifetime of a power source.

Figure 22:
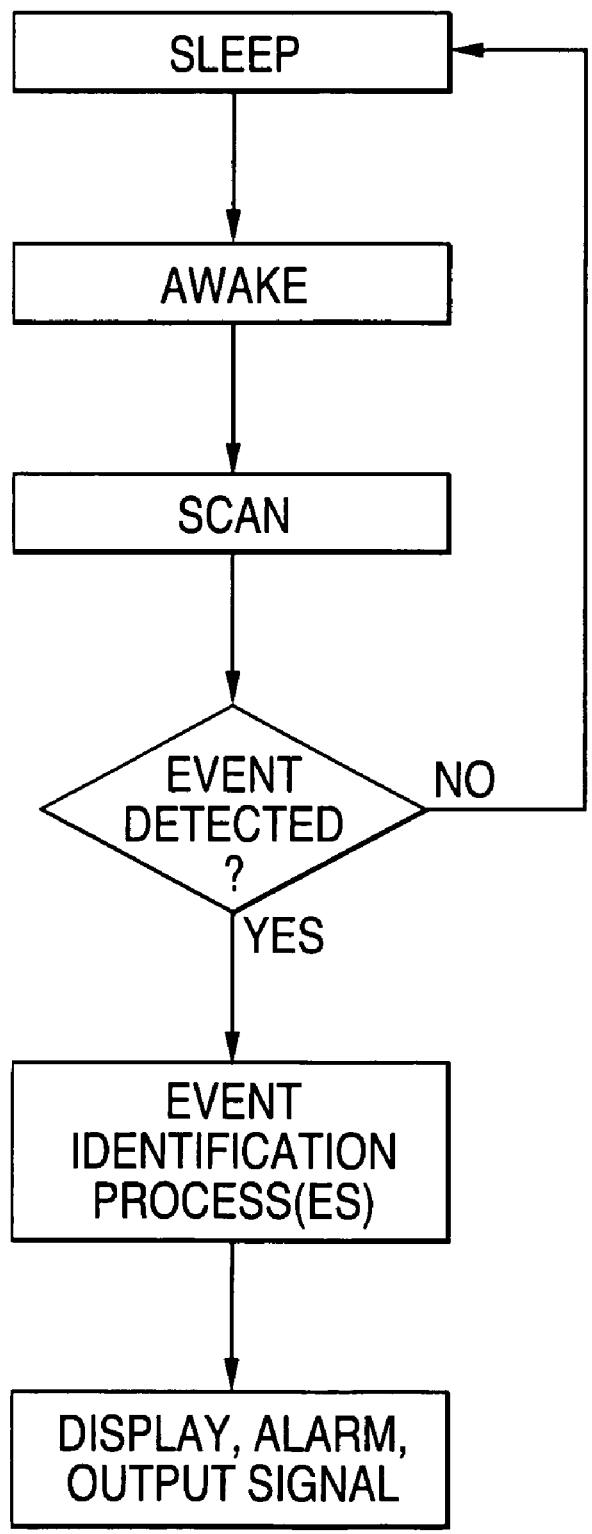
FIG. 22 illustrates a power management method according to one embodiment.

One goal of wearable badge devices is optimal power management. One embodiment of a power management method of the present invention is shown in FIG. 22. In one aspect, the device is placed in a SLEEP or very low power mode 200 for a significant amount of time, e.g., over 70%, or 80% or 90% of the time, depending on needed response time. The processor wakes up periodically 210, for example, in response to a wakeup signal from power supply circuitry 155, scans 220 across the sensor array and determines whether an event has occurred or is occurring 230. If not, the processor is put back to SLEEP 200. If an event is detected, the processor executes pattern recognition techniques 240 to identify the event. Once identified, the event is announced 250, e.g., either displayed, an output signal is activated, an audible alarm is activated, etc. or all of the above. Additional core average processing power is on the order of uA's.

Power Source

The device can be powered by a variety of means including an on-board battery or solar cell 145. Coin size batteries, such as standard 3 V batteries, are particularly useful and could last 5–10 years or more. The device might also be configured with an RF or IR tag element or module 150, whereby optical radiation or electromagnetic energy (activation energy signal) is remotely delivered to the device. In RF or IR tag embodiments, the device instantaneously stores enough energy from the activation energy signal to process information and relays this information back to the power source. Aspects of useful RF and IR tag circuitry can be found in U.S. Patent Application Ser. No. 60/477,624, filed Jun. 10, 2003, entitled "Chemical Passive Sensor", the contents of which are hereby incorporated by reference.

Self-c1041 alibration

In certain aspects, the system is configured to periodically monitor all physical channels and determine if the sensor inputs are within the electrical operating range. If not, the system automatically biases each sensor accordingly and adjusts its baseline readings.

Event Detection

Event Detection is implemented to further reduce overall power consumption. In one aspect, an event first detected, then pattern recognition methods are used to identify the event(s). Event detection is threshold-based in one aspect. For example, in one aspect, once an event is detected the on-board processor is awakened (interrupted) and one or more pattern recognition processes are executed to identify the event.

Figure 23:
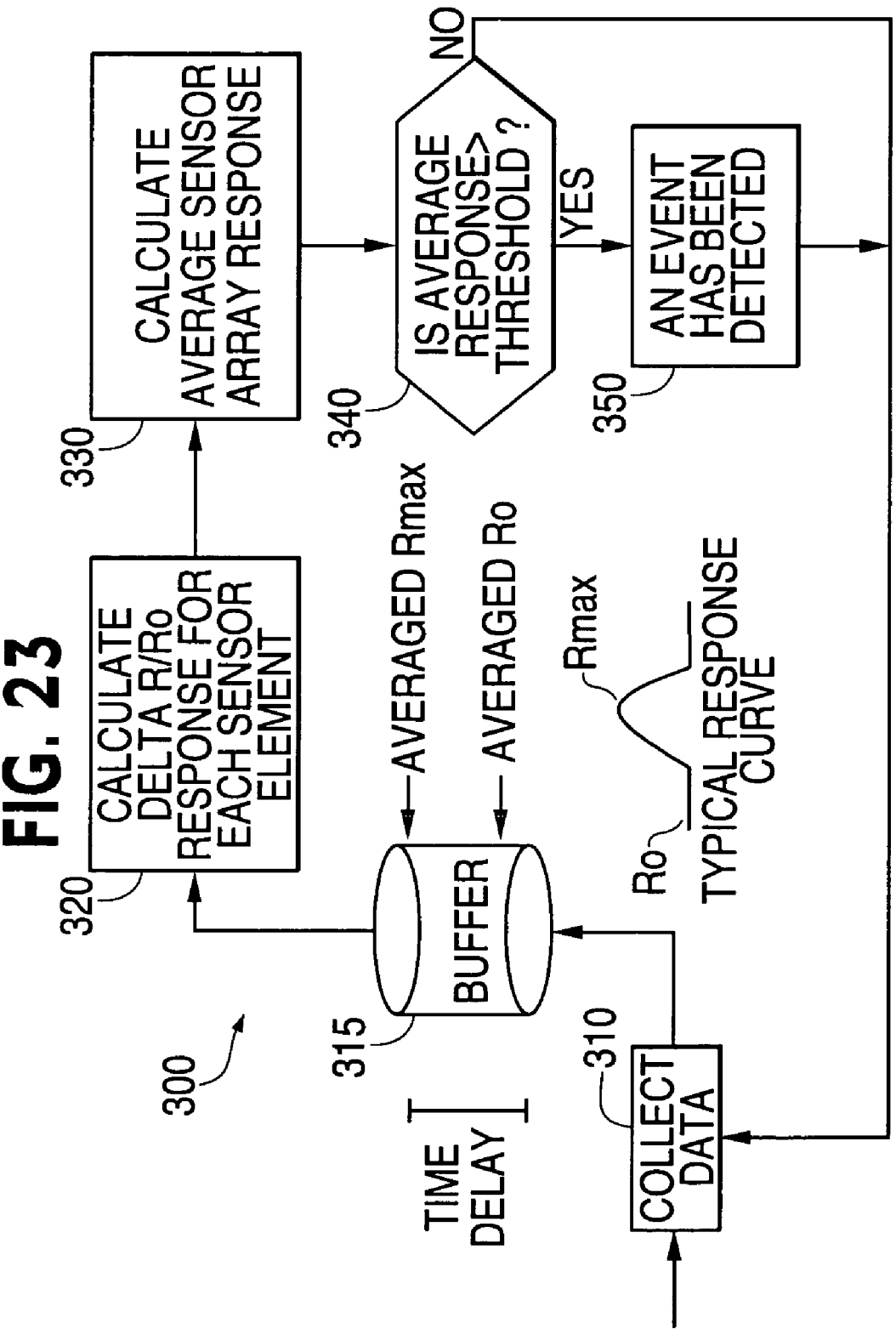
FIG. 23 illustrates a detection process and a typical response curve according to one embodiment.

FIG. 23 is a generic block diagram illustrating a detection process 300 and a typical response curve according to one embodiment. In the following description of aspects of process 300, process parameters such as delay time, average response and threshold have been chosen based on experimental results and are only meant to be exemplary and not limiting in any way.

Data is first collected 310 from each of the sensors, e.g., sensor response signals are collected. Each sensor response signal represents a resistive measurement in the case of PCS sensors. The resistance changes depending on the type of event to which the sensor is exposed. Each sensor element preferably responds in a different fashion. In one aspect, the process 300 allows for a moving base resistance; the response is the percent change from the most recent measurement with respect to a past moving base resistance. In one aspect, a circular buffered, backward-looking moving average process is coded and implemented in the on-board processor. The buffered data represents a time parameter to store the baseline resistance of each of the channels, e.g., number of sensors in an array.

The baseline resistance of all sensors is calculated 315. To account for slow changes in ambient conditions, such as humidity and temperature, and any sensor drift, the baseline resistance, $R_0$, is constantly updated based on recent history. There are at least two parameters—delay time and averaging time—that can be tuned. Since the data in one analysis was acquired over a short period of time, the delay time (or buffer) was set at 200 points (~2 minutes) and averaging time was set at 5 points.

The response of all sensors is calculated 320. In one aspect, the response, $\Delta R/R_0$, is calculated for all sensors as a fractional change in resistance, $$\Delta R/R_0 = \frac{R(t) - R_0}{R_0},$$

where R(t) is the time-averaged resistance at the present time and $R_0$ is the baseline resistance collected at 2 minutes earlier. The responses for individual sensors are used for pattern recognition to identify an event, e.g., determine whether a disturbance is a nuisance or a fire.

The sensor-averaged response is calculated 330: In one aspect, the sensor-averaged response, $(\Delta R/R_0)_{avg}$, is calculated to provide a robust measurement of the presence or non-presence of a disturbance.

The sensor averaged response is compared with a threshold value 340. In one aspect, for example, if $|(\Delta R/R_0)_{avg}|>$ 0.001 (or other threshold value, e.g., 0.01), then the magnitude of the sensor-averaged response is too large indicating that an event has been detected, e.g., a disturbance from normal operation has been detected. The threshold value may be preset and adjustable. It is necessary to evaluate the magnitude of the disturbance since sensor responses increase and decrease with a change in an environmental state or in the presence of an environmental condition such as a fire. If no disturbance is detected, normal operation is continued.

Pattern Recognition

Once an event has been detected 350, the processor awakes from SLEEP (see, e.g., FIG. 22). The responses from all channels are temporarily stored in memory, e.g., RAM, and compared to known chemical patterns. Simple to very complex pattern recognition techniques might be implemented depending on the application. Such techniques include K-nearest neighbor (KNN), Canonical Discriminate Analysis (CDA), Soft Independent Modeling of Class Analogy (SIMCA), probabilistic neural network (PNN), artificial neural network (ANN), support vector machine (SVM), Fisher Linear Discriminate (FLD) and others.

In wearable badge embodiments, a detector badge would be worn by an individual, e.g., attached to a lapel or shirt or pants pocket with an integrated clip or pin, or worn around the neck, and when powered on would notify the wearer of normal detector status (e.g., green LED, no alarm) and battery status (e.g., green/red LED). After status check, the detector badge would monitor the environment continuously and announce detected hazard events, e.g., via an audible, visual (e.g., red LED) and/or vibratory alarm. Detector badges might also include modules for recording data and wirelessly transmitting information such as badge ID, status information and alarm condition information, to a central monitor station. Detector standardization using a supplied standard to verify proper operation, either periodically or before use, and battery replacement or recharging are typically user maintenance activities that may be required.

Wireless portable detectors without pneumatic system 35 can be implemented for applications that have stringent requirements for size, cost, power requirements and ruggedness. Such scaled down detectors are useful as badge detectors for TICs, BWAs and CWAs. Additionally, communication module 30 can be eliminated for badge devices where a personal alarm is the only necessary feedback.

In certain aspects, a modular detector device is provided. For example, a detector device or sensor module may be coupled to a communication module. For example, a badge device in one aspect is configured to plug into a thin communications platform that allows the detector device to be included in a distributed network. The platform can include wireless or wired network connections. A sensor module can couple with any additional modules such as pnuemnatics, communication, calibration, power recharge and other modules. As another example, a detector device can be implemented as a residual life indicator, e.g., by inserting the device in a respirator cartridge as will be discussed in more detail below.

Event Detection and Analysis

In preferred aspects, digital signal processing (DSP) unit 20 incorporated in the detector device converts the sensor responses into an actionable answer. At least three different classes of techniques may be used, depending on the requirements of the application. These classes are listed in increasing order of complexity:

Simple detection: Thresholds are applied to individual sensors or globally to the responses of the entire array. When the threshold logic is satisfied, an alarm condition is detected. For example, if any of four sensors in an array exceeds a threshold value, an alarm activates, e.g., alarm 25 is activated.

Pattern recognition: The response pattern from the array is compared to patterns stored in a training set or library. When a match is found, the identity of the vapor is returned. Useful pattern recognition techniques include KNN, CDA, SIMCA, PNN, ANN, SVM, FLD and others.

Quantification: The response pattern from the array is used in certain aspects to calculate the concentration of analyte in the vapor phase.

In certain aspects these techniques can be used individually or mixed-and-matched. For example, simple detection can be used to detect that an event is occurring, and pattern recognition can be used after event detection to identify the nature or source of the event. Such a DSP methodology has been used successfully in a passive sensor array such as in a fire detector in UL and BSI laboratory tests.

For chemical events, the minimum detectable levels of the detector devices are important since the IDLH level has been identified as a requirement for consistently detecting the presence of TICs and CWAs. In certain aspects, the minimum detectable level (MDL) of a single sensor is measured by its detection limit. A detection limit is a useful concept to describe the performance of an analyte-specific sensor and is typically defined as the concentration that yields a sensor response with a signal-to-noise ratio equal to a threshold value (e.g., three). A detection limit is appropriate for analyte-specific sensors since few other chemicals could have caused the same level of response. If a detection limit is applied to a single sensor in an analyte-general array, any chemical could have caused the response since the sensor does not have specificity. Discrimination limits and identification limits are more useful concepts when describing the performance of an analyte-general sensor array. The discrimination limit is defined as the analyte concentration at which a method of pattern recognition can be used to discriminate an analyte in a carrier gas from the carrier gas alone. The identification limit is defined as the analyte concentration at which a method of pattern recognition can be used to consistently identify the presence of an analyte. An identification limit is preferably used as the measurement of performance for the MDL in certain aspects.

Since equation (2) is valid for individual polymer-composite sensors, this equation can be used with experimental data for chemical species to estimate the MDL of the sensor array for any other chemical. FIG. 2 shows IDLH concentrations on a plot of concentration versus vapor pressure for CWAs and TICs. In FIG. 2, the sensor array has a high probability of identifying any analyte with a symbol above the region labeled "Minimum detectable levels for sensors in C320 (estimate)." This region will be called the region for minimum detectable levels (RMDL). The sensor array has moderate or low probability of identifying an analyte with a symbol inside or below the RMDL, respectively. The further below the RMDL, the probability of identifying the vapor decreases.

A region is preferably used for the MDLs rather than a single line for the following reasons:

Variability of environmental conditions: Applications that have environments that are more variable tend to have higher values for minimum detectable levels. The applications tend to have minimum detectable limits closer to line A.

Sample variability: Applications that have analytes with significant variability also have higher values for minimum detectable levels. These applications typically include natural products and tend to have minimum detectable limits closer to line A.

Application-specific sensor array: When a specific application is identified, specific sensors can be used (or sensor responses can be removed in software) to remove unimportant information, and sensor performance improves. Application-specific sensor arrays tend have lower values for minimum detectable levels closer to line B.

For badge detector devices, the MDL is generally closer to line B on FIG. 2. The two effects of variability are approximately equal and have opposite effects. Since a badge detector is a field-use device, environmental variability tends to increase the MDL, but sample variability is small since the chemicals are well defined, causing the MDL to decrease. Since applications tend to focus on CWAs and some TICs, the MDL can be improved by using the most appropriate sensor array for the application.

Tests of the C320 further validate the estimates in FIG. 2. During controlled tests of CWAs by independent laboratories (Midwest Research Institute and Battelle Memorial Institute), sensor arrays in the C320 detected Tabun (GA), Sarin (GB), Soman (GD), VX, Sulfur Mustard (HD) and Nitrogen Mustard (HN3) at or below a 9 ppbv threshold limit. Additional testing by the U.S. Army Edgewood Chemical and Biological Center showed the C320 correctly discriminated GB, GD, VX, HD, Malathion and DMMP.

Detector devices according to the present invention are also capable of identifying and discriminating narcotics, explosives (e.g., TNT, C4, RDX, ANFO and others) and hazardous materials.

Analyte-general chemical alert devices of the present invention are advantageously capable of detecting biological and chemical hazard events arising from a wide range of chemical and biological classes and are not restricted to a pre-defined short-list of just a few TICs. In certain aspects, effects of interference and cross-reactivity are minimized through a combination of sensor materials and detector operational design (algorithm and hardware) as described above using event detection, discrimination and interferent rejection techniques. 1) Event detection: Changes in environment (false positives) due to temperature, humidity, or chemical background occur gradually, over minutes to hours, and are not recognized as hazard events. Second, polymer-composite sensors (PCS) are not dosimeters; cumulative low-level exposure over hours/days will not trigger an alarm (unlike colorimetric indicators). Third, the polymer-composite (PCS) sensors are stable and less reactive to moisture than other sensors (e.g., conducting polymers). The combination of PCS sensors and event detection helps minimize false positive risks. 2) Discrimination: Real-time pattern-recognition techniques are preferably used to identify chemical classes. Although unrecognized chemicals may not register a class alarm (false negative), a two-stage approach minimizes the risk of false negatives by utilization of chemical event detection followed by discrimination. In this case, even new and unknown threat chemicals will register an event alarm for hazards above a threshold. 3) Interferent Rejection: In addition, real-time pattern recognition is preferably used to screen for and reject known interferents that may otherwise register as a chemical event, e.g., sudden increase in moisture content due to sea spray, spills or cleaning operations.

In wearable badge detector embodiments, polymer-composite sensor arrays are particularly advantageous as they are preferably 1) rugged and stable in various environments; 2) compact, lightweight and wearable; 3) inexpensive to produce; and 4) low power consumption systems. More detail about such advantages follows:

Rugged and Stable: Polymer-composite sensors are stable in the presence of moisture, allowing the sensor array to operate over a wide range of humidity (0–99%, noncondensing). PCS sensor arrays have been tested in aqueous solutions for nearly 5,000 continuous hours with no effect on sensor stability. The array also operates over a wide range of temperatures. Tests have been completed over a temperature range of −15° C. to 40° C. with no effect on the sensors. Finally, the array has a long shelf life. Sensor arrays have been stored for up to three years in an uncontrolled environment in a laboratory, and the arrays required no special pretreatment before use.

Compact, Lightweight, and Wearable: The chip can be implemented using dimensions of approximately 1.25"×1.25"×0.25" with a mass of a few ounces. In preferred aspects, the chip, and hence the device in some embodiments, has a footprint area of less than about 4 square inches (e.g., 2"×2") and more preferably less than about 1 square inch (e.g., (1"×1"). The chip includes processors, battery, and sensors. Further miniaturization can be achieved, if required.

Inexpensive: The polymer-composite sensor array is inexpensive because the sensors are comprised of small amounts of carbon black and COTS polymers. The direct cost for sensor materials is very low, e.g., significantly less than $0.01.

Low Power: Polymer-composite sensors require only μW of power during normal operation. The chip can operate for at least six months or more using a typical battery.

Figure 5:
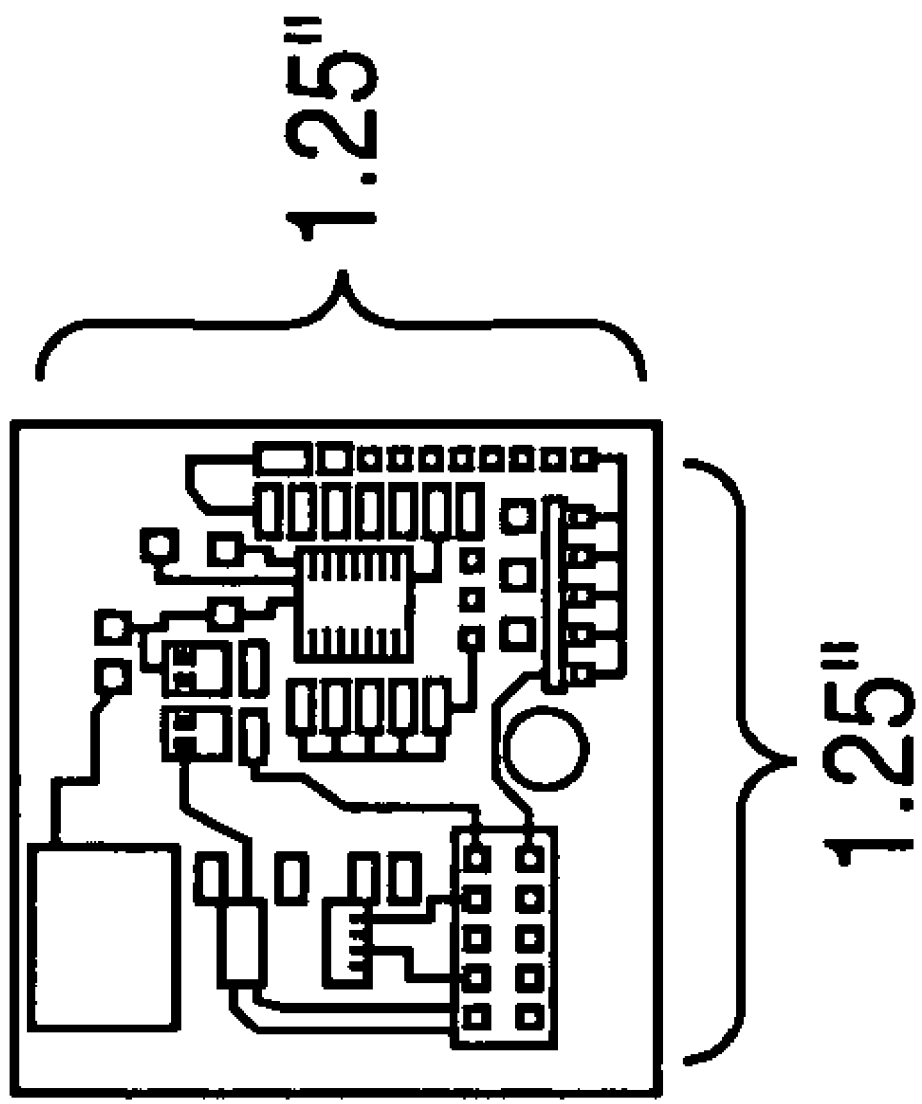
FIG. 5 shows an example of a detector device according to an embodiment of the present invention. In this instance and by way of example only, the detector device is a four-channel chemical event detector.

In one embodiment, a four channel detector, operating in a variable humidity environment, detects transient chemical events (malodors) of unknown composition and triggers an alarm/response via an RF link when a programmable threshold value is exceeded. In one aspect, no data is transmitted from the sensor, just an alarm state. A typical response curve to a transient event is shown in FIG. 4 for such a device, and an example of such a device is shown in FIG. 5; the backside contains the battery and the antenna. In a preferred badge embodiment, there is no pneumatic system and the detectors are continuously exposed to the environment.

Fire Detection and Prevention

Figure 6:
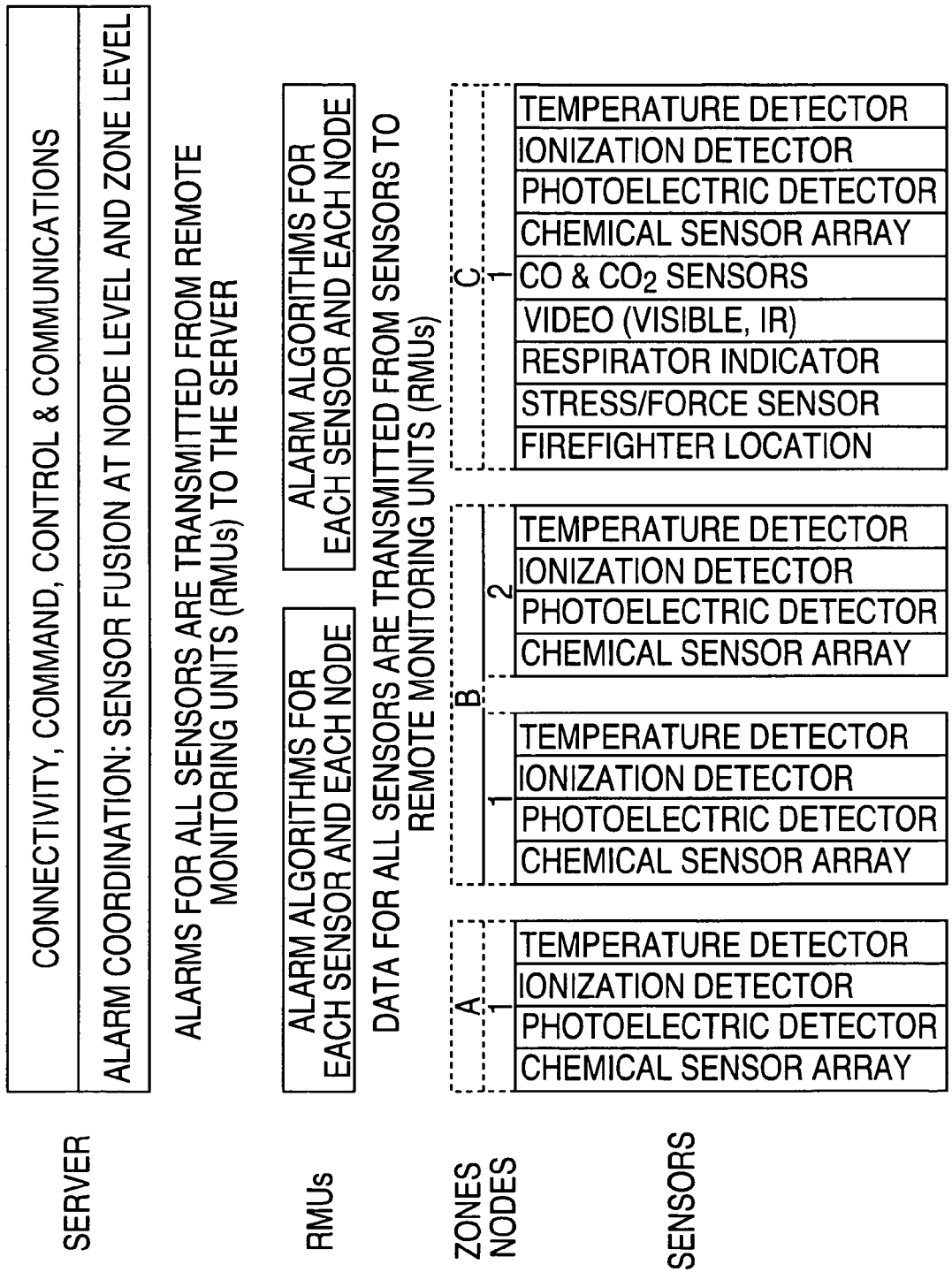
FIG. 6 shows an example of a fire detection system including detection devices according to an embodiment of the present invention. In this instance, the nodes are defined as a collection of sensors/detectors at a single physical location, while the zones are defined by physical relationships between the nodes. This, in this instance, provides a mulit-level architecture for data analysis which renders the system both flexible and scalable.

In certain aspects, devices according to the present invention are particularly useful in fire detection and prevention activities. In such embodiments, devices of the present invention preferably include a PCS array and one or more additional sensor modules such as a photodetector, an ionization detector and a thermal detector. Published PCT Application WO00/79243, which is hereby incorporated by reference for all purposes, discloses sensor systems including multiple sensor types which are useful for fire detection and prevention applications as well as for other detection applications as described herein. Signals from the PCS array and other included sensors are monitored and processed by an algorithm configured to detect events and nuisances and discriminate between fire sources and nuisance sources with a high degree of confidence so as to reduce the occurrence of false positives. FIG. 6 shows an example of a fire detection system including detection devices according to an embodiment of the present invention.

Many current chemical sensor arrays can discriminate different types of fires after the fire has been active for a long period of time. However, this use-model is not adequate for fire detection since time is of the essence. According to the present invention, an algorithm detects an event as early as possible and immediately identifies the event as a nuisance or fire. In the section following, examples of fire and nuisance data are disclosed:

Fire & Nuisance Data

TABLE 1

Fire tests that were completed in fire room.

| UL Fire Tests | BSI Fire Tests | Non-Standard Fire Tests |
|---|---|---|
| Gasoline 1 | Alcohol 1 | Dense plastic fabric |
| Gasoline 2 | Alcohol 2 | Flaming cotton fabric |
| Heptane 1 | Cotton 1 | Plastic curtain |
| Heptane 2 | Cotton 2 | Smoldering cotton 1 |
| Paper 1 | Flaming Wood 1 | Smoldering cotton 2 |
| Paper 2 | Flaming Wood 2 | Smoldering linen & plastic |
| Polystyrene 1 | Heptane 1 | Smoldering paper 1 |
| Polystyrene 2 | Heptane 2 | Smoldering paper 2 |
| Smoldering Wood 1 | Polyurethane 1 | Smoldering paper 3 |
| Smoldering Wood 2 | Polyurethane 2 | Smoldering cotton fabric |
| Wood Crib 1 | Smoldering Wood 1 | |
| Wood Crib 2 | Smoldering Wood 2 | |
| Smoldering | | |

TABLE 2

Nuisance tests.

| Series 1 | Series 2 |
|---|---|
| Bacon, open door | Bacon |
| Cigarette on pillow | Cigarette 1 |
| Floor buffing | Cigarette 2 |
| Fries cooking | Cigarette puffs |
| Oil, open door | Dry air freshener |
| Oil | Enamel |
| Sour craut | Nilotron |
| Steam | Popcorn |
| Sugar | Rustoleum |
| | Varnish |
| | Wall Paint |

In one embodiment, simple detection is used to detect that an event is occurring, and pattern recognition is then used to identify the nature of the event. This two-tiered algorithmic approach for detecting and identifying events works well for polymer-composite sensor arrays. The first algorithm simply detects that an event occurs. All fires must be detected, and, ideally, no nuisances would be detected. But it does not matter whether the event is a fire or a nuisance at this point because the second algorithm is used to differentiate between these two groups of events.

There are several parameters in the detection algorithm that are preferably optimized so that all fires are detected and a minimal number of nuisances are detected.

These parameters include:
  type and number of sensors used for averaging;
  number of points used for time averaging;
  number of points in the buffer (delay time);
  the number of consecutive points outside the threshold; and
  the value of the detection threshold.

Figure 7:
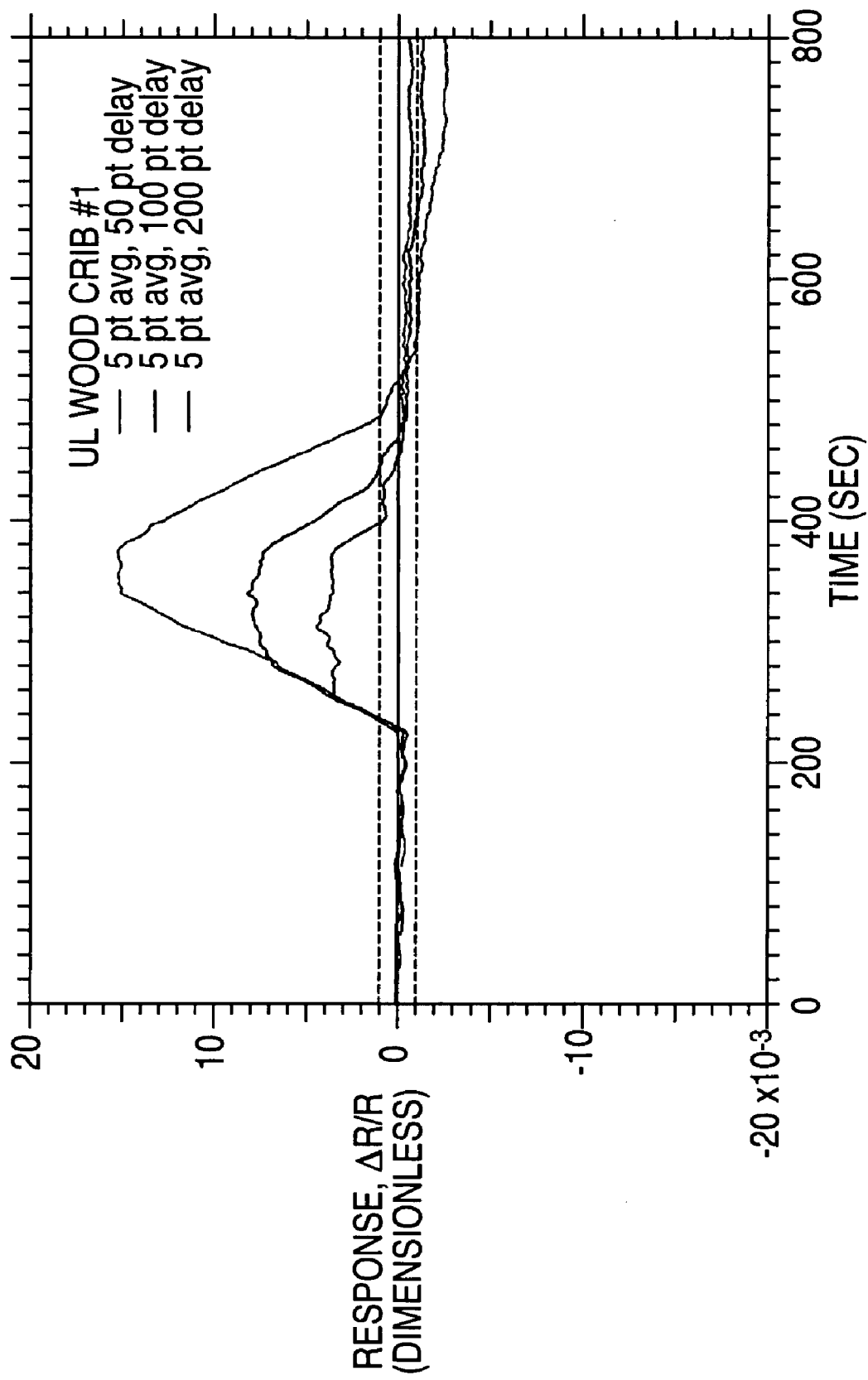
FIG. 7 shows a typical response for a device using 32 sensors. The graph shows response as a function of time for the UL Wood Crib #1 fire.

A typical response is shown in FIG. 7 using an array of 32 PCS sensors when all 32 sensors are used and the number of points in the buffer is a parameter. The parameter had little effect on the detection time, but the number of buffer points drastically affected the overall magnitude of the response.

Figure 8:
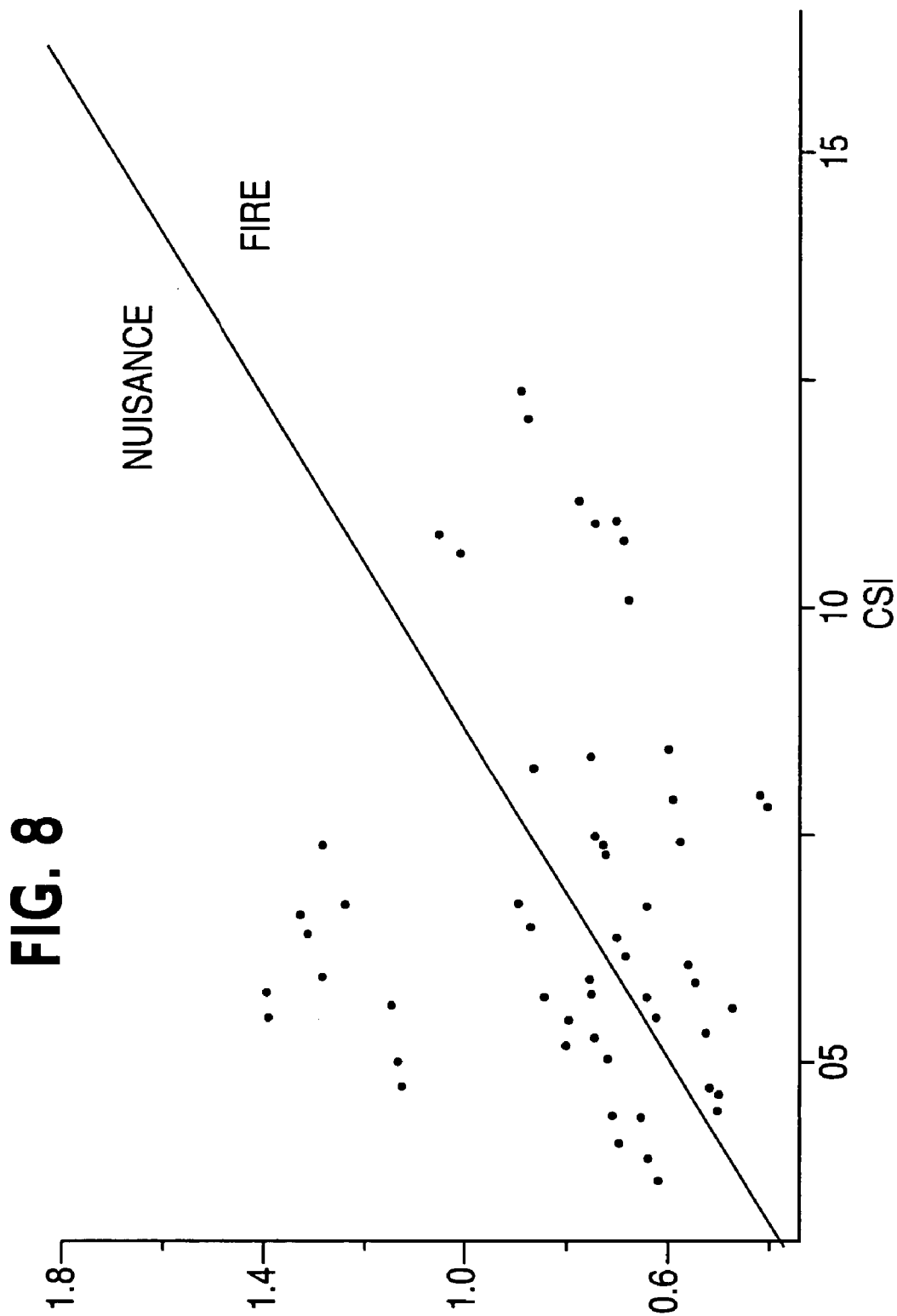
FIG. 8 illustrates a model using Soft Independent Modeling of Class Analogy (SIMCA). In this instance the model is, merely by way of example, for fire and nuisance tests that exceed a positive threshold. The line seperating these two regions is drawn to minimize the number of false negatives such as the case wherein the actual event is, by way of example, a fire but no alarm is sounded.

Once an event is detected, the second part of the algorithm identifies the nature of the event as a fire or a nuisance. FIG. 8 illustrates a model using Soft Independent Modeling of Class Analogy (SIMCA).

Additional useful algorithms are disclosed in U.S. patent application Ser. No. 10/112,151, filed Mar. 29, 2002, the contents of which are hereby incorporated by reference for all purposes.

Protective Absorption Based Filters

In certain aspects, devices of the present invention are useful in protective absorption based filter systems. The actual useful life of a protective absorption based filter is a function of the amount of absorbent material, the absorbent-sorbed species interaction, and the concentration and duration of the exposure. Since this data is almost always unknown, the manufacturers' recommendations and civilian and military specifications are based on a few marker chemicals and test scenarios and offer only a rough guide as to when to replace or regenerate the filter. In most cases as well, the end user does not know when the exposure starts or ends, and what chemical's biologic agents and concentration levels are present in the environment. Sensor devices of the present invention incorporated into a filter or pneumatic pathway can provide a timely warning to the user that the absorptive capacity of the filter has reached a pre-defined level. This allows users to exit the hazardous area and replace or regenerate the media and reduce the potential hazard to these personnel. Accordingly, in one aspect, the present invention provides polymer-composite sensor arrays in protective air filtration systems so as to provide low-cost, low power, lightweight, rugged, stable, and accurate residual life indicators for personal protective air filtration systems for Volatile Organic Chemicals (VOCs), biological agents and other hazardous materials. Such systems are useful in, for example, filter breakthrough systems, indoor air quality applications, cabin air systems, personnel protective equipment and motor vehicles.

In one embodiment, multiple miniature sensor devices are positioned at various depths in a filter bed such that successive sensor detection of a breakthrough event (at the IDLH) level and subsequent alarm outputs correspond to consumption of the absorptive capacity, hence indicating residual life. The final sensor is preferably placed appropriately to permit some exit time from the hazardous area without undue wastage of filter cartridges.

Figure 11:
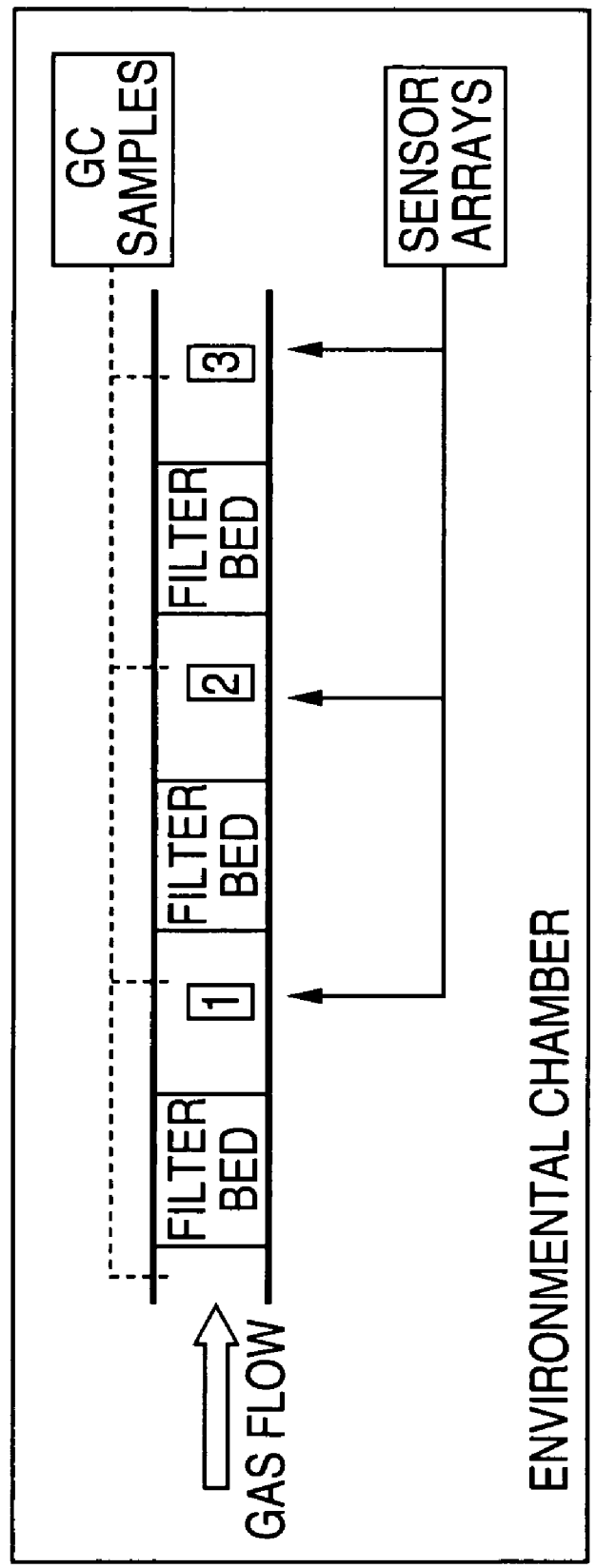
FIG. 11 illustrates a schematic representation of a Residual Life Indicator Fixture according to an embodiment of the present invention.

FIG. 11 illustrates a schematic representation of a Residual Life Indicator Fixture according to an embodiment of the present invention. As shown, detectors are sequentially positioned within a filter bed by embedding detectors in filter material in a gas flow path. Inlet and approximate stage-wise analyte concentration is monitored semi-continuously by Gas Chromatography and continuously by sensor output. The upstream sensor (1) responds to the presence of the analyte when the first Filter Bed experiences breakthrough while the still protected downstream sensors (2) and (3) do not respond. This is analogous to consumption of ⅓ of the filter system capacity (⅔ Life Remaining). As flow continues, downstream sensor (2) responds as the second Filter Bed experiences breakthrough; this corresponds to consumption of ⅔ of the filter system capacity (⅓ Life Remaining). The final filter bed also serves as the gas scrubber. The approximate stage-wise concentration in the filter bed is preferably monitored by Gas Chromatography as well as by the polymer-composite sensor system.

Figure 9:
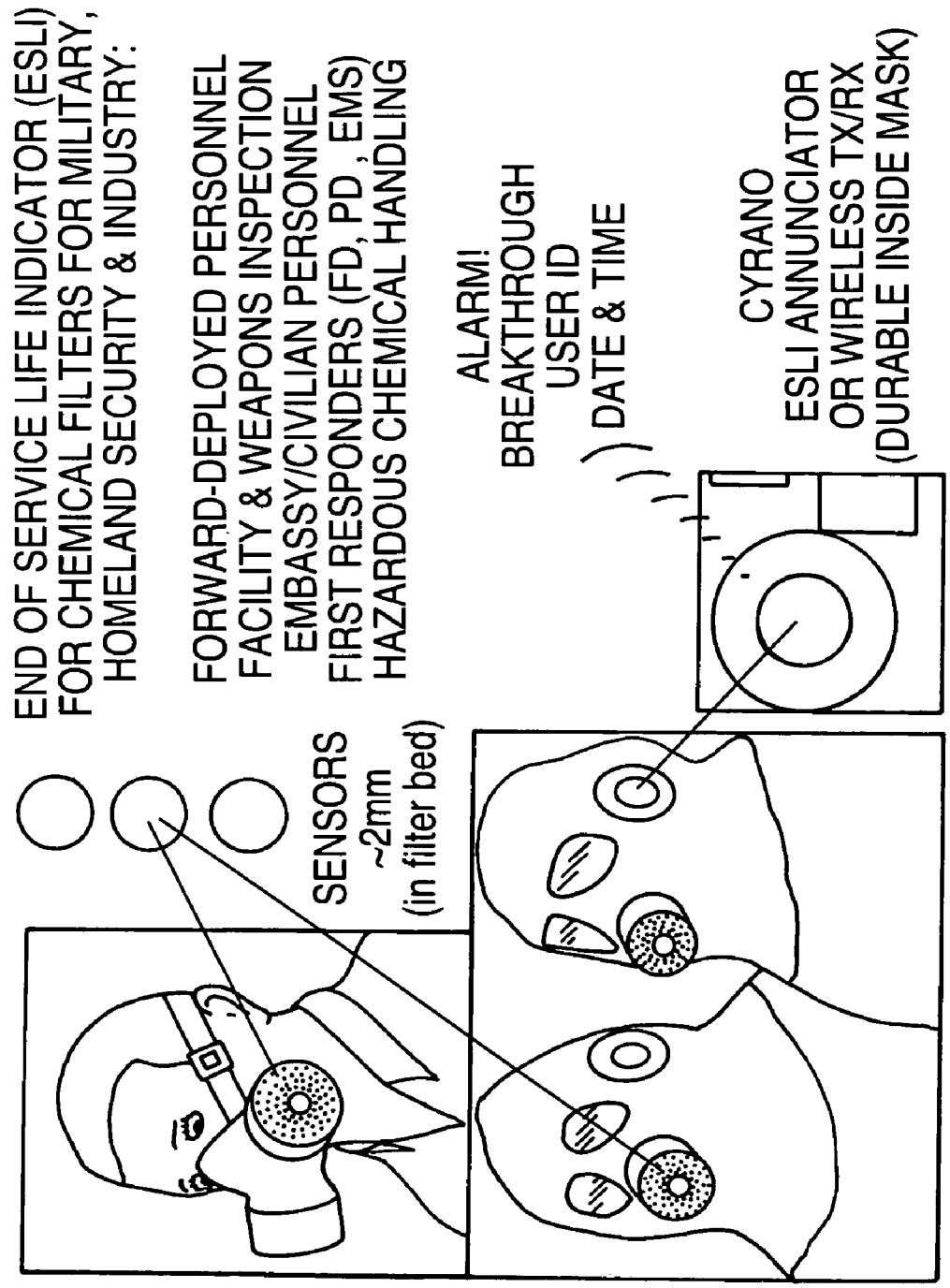
FIG. 9 llustrates examples of chemical filter systems for which an end-of-service-life indicator (ESLI) module including one or more PCS sensors are useful.

FIG. 9 illustrates examples of chemical filter systems for which an end-of-service-life indicator (ESLI) module including one or more PCS sensors is useful.

Figure 10:
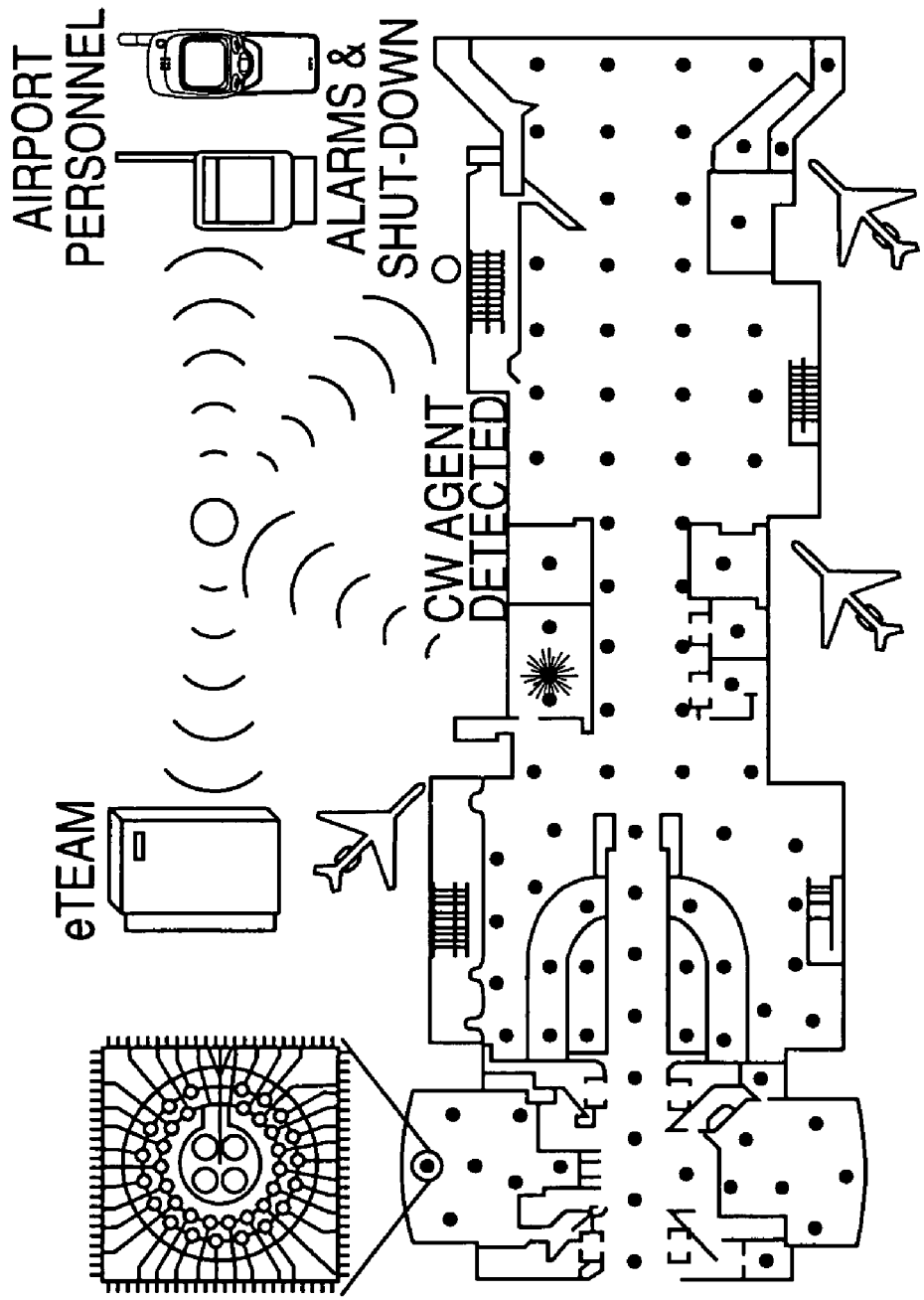
FIG. 10 illustrates a system for remote detection and notification in airport terminals including a distributed network of wireless sensor devices according to an embodiment of the present invention.

FIG. 10 illustrates a system including a distributed network of wireless sensor devices according to the present invention. The sensors shown can be implemented in air filtration or detection systems or as stand-alone devices positioned as desired. In one aspect, a population of sensing devices may be distributed randomly or in known locations to form a network. Each such device preferably includes a transceiver or other wireless communication module for communicating information signals to a base intelligence node, such as a central processing node, central computing device or distributed network of computers and or processing nodes. The base intelligence node receives and processes signals received from the various sensing nodes and provides valuable information therefrom to an operator, or may automatically activate an alarm if a threshold condition is met. In some aspects, the sensing devices include GPS (global positioning system) location modules or other location determining modules to determine the locations of the devices. Location determining modules are particularly useful where sensing devices are randomly distributed, e.g., dropped from an airplane or otherwise randomly, geographically distributed, and it is desirable to associate a precise (previously unknown) location with a detected event, agent or environmental parameter. For example, a growing risk of asymmetric attacks has increased the need for distributed biological detectors with superior false positive rates relative to current solutions. The low cost, low power and highly sensitive chemical and biologic detectors of the present invention are capable of continuous distributed monitoring of biological warfare agents (BWAs) and will advantageously provide for improved monitoring of biological threats.

In one aspect, software processes are provided for both low level and high-level control of node function, for aggregating and interpreting sensor data at a single node, and for calibrating devices at the point of manufacture and in the field. In another aspect, a pattern matching approach is used to detect and identify compounds from a library. This library may reside either on the device or at a remote location. This approach allows for rapid upgrading of instruments as new threats become important.

A network of autonomous sensors reporting to a central location offers the potential to further false alarm reduction and improved alarm prediction through software processes deployed at the network level. In one aspect, therefore, processes are provided for sensor data fusion. One module of this system is a symbolic data model that reads discrete data (e.g. alarms, settings) and applies two different mathematical approaches to identify anomalies. In the first case, a set of rules is applied to this data to generate derived states and anomalies. While the mathematical analysis process may be generic, the set of rules must be determined for a given application so the SDM is best described as a "knowledge-based" component. For example, this portion should operate on rules such as: if alarm A sounds do nothing unless alarm B sounds. In addition to this rules based module, a second module is provided in some aspects which uses more advanced mathematical tools to identify anomalies. This module, in one aspect, utilizes Hidden Markov Models (HMM) to identify anomalies based on probabilities of passing from one state to a second state. The HMM may use different algorithms to define these probabilities such as a Viterbi algorithm, a forward-backward algorithm, or a Baum-Welsh algorithm. All of these methods are designed to find hidden patterns in data. The output is the prediction of an anomaly based on a number of different discrete state variables.

In networked systems, various network protocols may be used, such as for example, point-to-point, point-to-multipoint, and others. Devices and nodes may be individually addresses, and different networks may use a different pseudo-random hopping sequence. To prevent interfering collisions from different networks, modules may be configured to jump to different frequencies.

Figure 12:
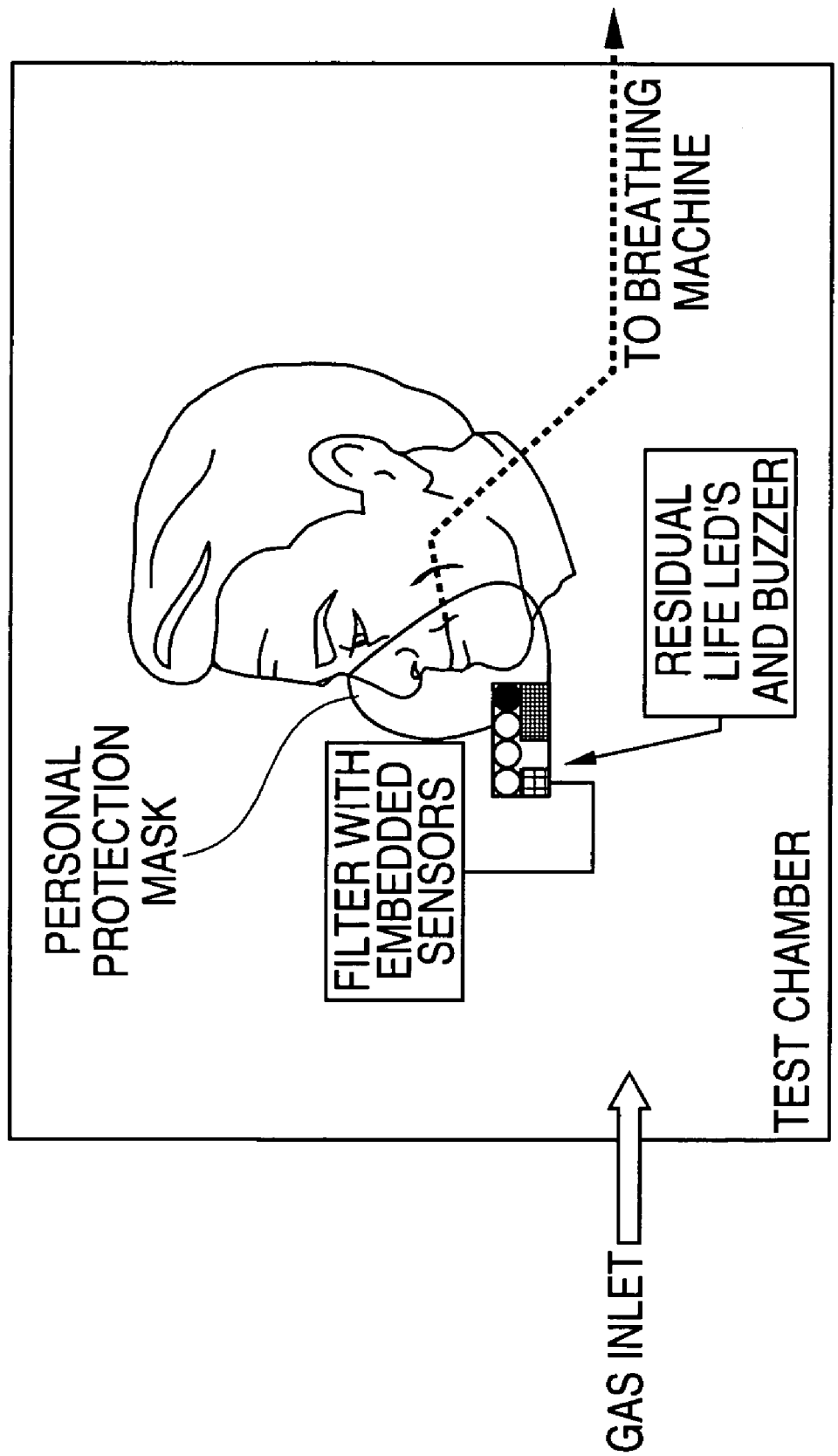
FIG. 12 illustrates a mask-based filter interface system including a detector device module according to an embodiment of the present invention.

FIG. 12 illustrates a mask-based filter interface system including a detector device module according to an embodiment of the present invention. The filter interface system communicates with the filter-based detectors and provides status/alarm output to the user based on filter status. The filter interface module is preferably configured to be mounted on the facemask and to contain the batteries, the signal processing circuitry and/or software and the visual and auditory alarms to indicate the status of the filter. Such placement allows the durable electronics to be placed in the mask and reused, thereby minimizing the operating cost (filters) of the system. Battery power usage is minimized while providing both visual and auditory cues to increase assurance of user notification in a noisy industrial environment. Size and weight is advantageously minimized using the detector devices of the present invention so as to not increase user discomfort and discourage use of the enhanced protective system.

In one embodiment, the present invention provides automated laboratory systems for detection of biologic agents. In one aspect, an automated inoculation and growth system is provided to interface with the existing BioWatch network and a wireless infrastructure is provided to communicate relevant information back to a central location. In another aspect, a laboratory system is provided which automates the inoculation and growth of collected samples, measures these samples with an array based sensor and uniquely reports the presence and identity of the micro-organisms with high reliability.

Laboratory identification of bioterrorism agents typically requires confirmation by visual and chemical means. Standard procedures require growth of live cells for 24 to 48 hrs followed by examination of the developed colonies for particular morphological (size, shape) and chemical characteristics (gram+/−stains, antibiotic susceptibility). While this technique is time consuming, it is the "gold standard" for positive confirmation of a biological agent.

Figure 24A:
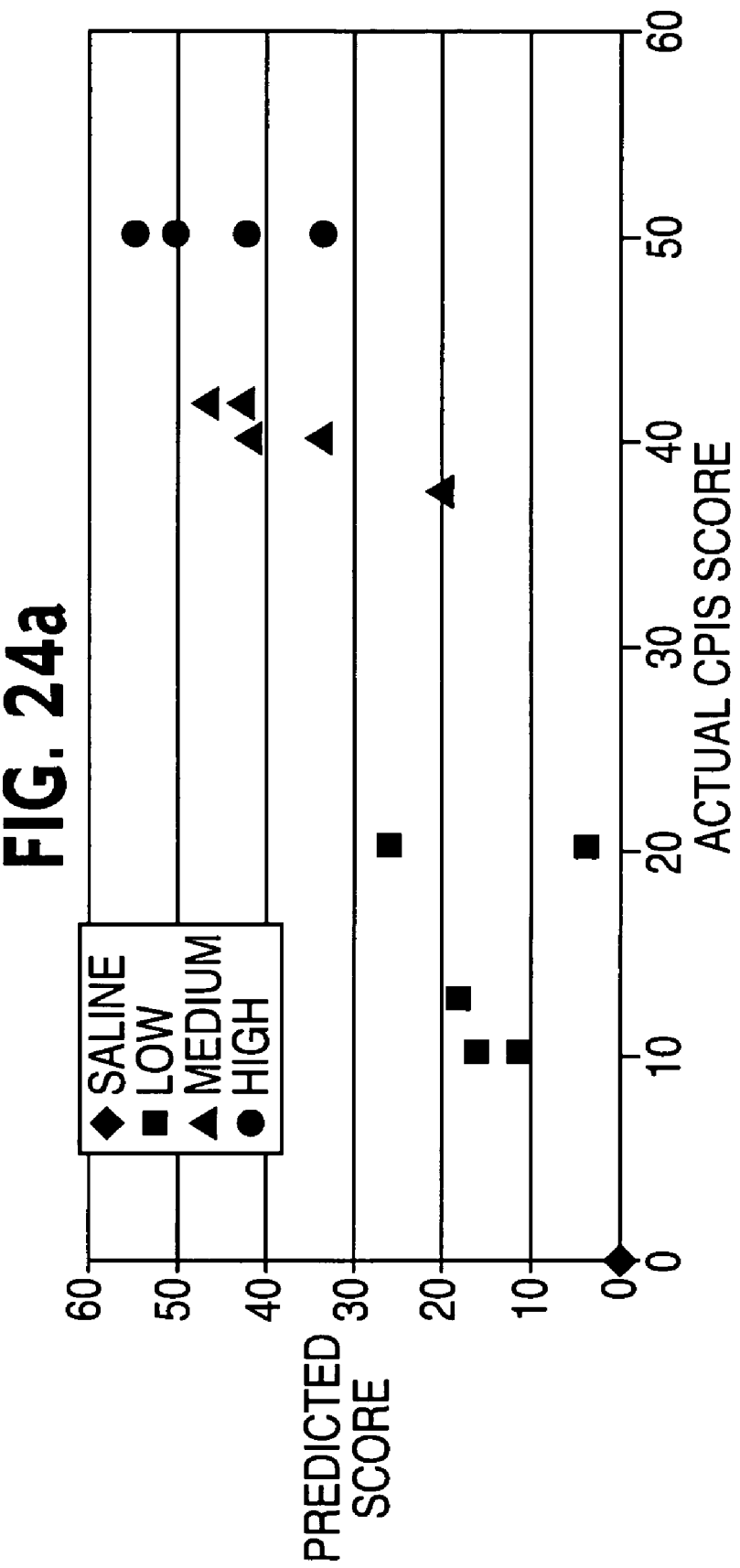
FIG. 24a shows the correlation between traditional and breath-based diagnoses.

It is well known that growing micro-organisms produce metabolites that are characteristic of the growing organism. This identification of micro-organisms from their growth metabolites has traiditonally been accomplished using gas chromatography (GC) and/or mass spectroscopy (MS). Recently, Cyrano has demonstrated that measuring the volatile metabolites of cell growth using a hand held array based detector can also be used for discriminating *B. anthracis* (BA) in tests conducted by the Midwest Research Institute on standard growth medium (TSA). The test results show detection in as little as 3 hours using standard growth media is feasible. Discrimination from other bacteria species (*E. coli*) and negative controls was also clearly demonstrated. See FIG. 24a. A new medium, 3AT, was developed for rapid growth and isolation of BA by the Air Force Research Laboratory (WPAFB, Ohio). Medium 3AT produces a five-fold increase in BA growth rate, yielding 24 hrs growth in as little as 5–6 hrs. Combined with the prior Cyrano results, detection of BA from spores is possible in less than 1 hour. Further refinements of the medium may be possible to yield even faster results and specific growth of Bacillus species, to the exclusion of other spore-forming bacteria and non-bacterial microorganisms. The technique is also easily extended to other micro-organisms.

Biological samples are already being collected as part of the BioWatch program. This system requires daily manual retrieval of filters which are analyzed in the CDC's Laboratory Response Network (LRN) laboratories. The standard analysis to confirm the presence of a wide range of biological warfare agents (BWAs) is microbiology. These protocols are publically available. In one aspect, this microbiological assay is used as the underlying detection means in a near real time system. The collected samples from the BioWatch system are grown in highly optimized growth media designed to rapidly promote the growth of BWAs while suppressing growth of traditional micro-organisms. The metabolites are measured from the headspace above the growth media at defined intervals after inoculation. Testing begins, in one aspect, 30 minutes after inoculation and continues for up to 24 hours. In this way, the initial answer that may be generated at very short time frames can automatically be confirmed on the same sample. Since continued growth generally leads to larger populations of the target bacteria, any initial alarms can be tracked and verified. Furthermore, because the technique uses standard microbial growth as the basis for the measurement, laboratory confirmation of any suspected positive result will not require any additional time for growth or amplification of the suspected micro-organism. Also, samples can easily be stored in the same growth media for up to five days and the organisms will still be viable.

In one aspect, current state of the art growth media is used to determine the earliest possible detection of agents, e.g. 20 agents from the CDC's Category A and B agents list. For each agent, growth media and growth conditions are optimized and the chemical nature of the metabolites is determined by GC or GC/MS. Simultaneous with the analytical assessment, measurements of headspace metabolites will also be carried out using nanocomposite array based sensor(s). The GC/MS data is then utilized to further optimize the sensors on the array and to determine optimal measurement times for the array. These measurements may be carried out as a function of time, growth media, initial inoculum size, and growth conditions. Results for live bioagents or simulants can be compared with samples obtained from environmental sampling and receiver operator characterization (ROC) curves can be produced and a false positive and false negative rate can be calculated.

In one aspect, a mechanical system is provided for automated inoculation, storage, and measurement. Since the amount of headspace required for measurement can be very small (<3 ccs), in one aspect, the system uses a titer plate like geometry as growth wells. In this way, standard pick and place instrumentation developed for high scale laboratory testing may be utilized as part of the system and any new development of mechanical tasks will be minimized. Since both aerobic and anaerobic growth may be required for each sample, the system makes provisions for providing all necessary growth conditions to create rapid and reliable bacterial growth.

In one aspect, an integrated laboratory system is provided that takes collected samples, introduces them into a growth media in a titer plate, automatically delivers the titer plate to a growth chamber and determines the nature and identity of any micro-organism growth. Samples with 0–10,000 organisms may be generated and time to positive prediction may be determined for multiple BWAs, e.g., at least 10 BWAs or BWA simulants. Receiver operating characteristics (ROC) curves may be generated.

Sensor Arrays

In certain aspects, multiple sensor types are integrated into a high density platform, preferably on a silicon chip, or other substrate material as is well known. In preferred aspects, the sensors are integrated onto a single chip. In addition to polymer-composite and conducting polymers, useful sensor materials include, for example, nanoscale polymer composites, carbon nanotube composites, nanogold composites, intrinsically conducting polymers, sol-gel biosensors based on intrinsically conducting polymers (e.g., sol-gel encapsulated enzyme based sensors), biopolymers such as self assembling monolayer (SAM) materials and others.

Advantages of such high density arrays include the ability to construct systems with largely varying sensor properties, and the ability to include a high degree of redundancy (both features of the human system). One significant benefit of redundancy is root n noise reduction, where n is the number of identical sensor elements. For example, the inclusion of 64 identical sensors produces an overall signal to noise ratio approximately 8 times that of a single sensor (see FIG. 13). Sensor arrays that are at least an order of magnitude more sensitive than those previously produced can thus be achieved through the incorporation of high degrees of redundancy. Such redundancy also has additional benefits in terms of long-term stability and overall robustness of the system.

Figure 13:
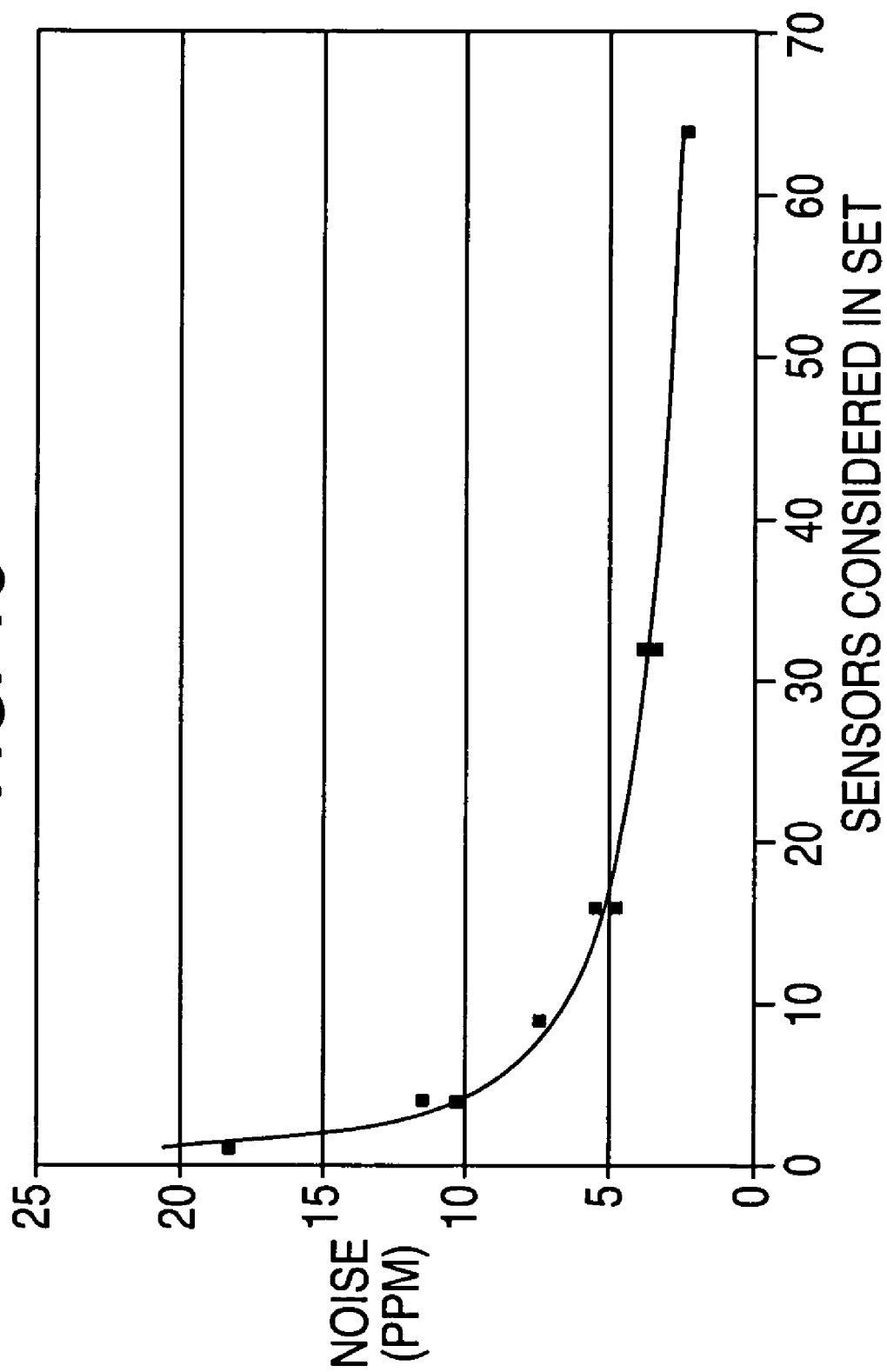
FIG. 13 shows signal to noise ratio measurements for multiple sensors.
Figure 14:
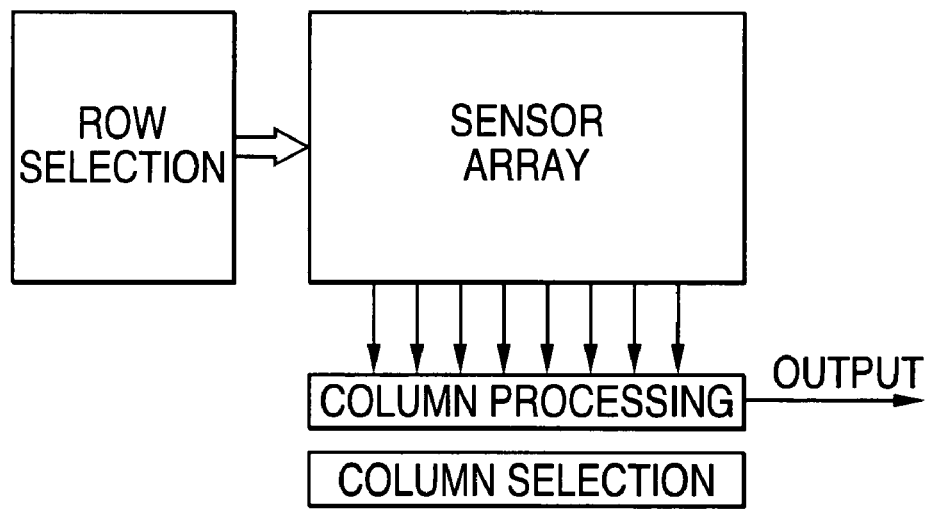
FIG. 14 shows addressing for a sensor array according to one embodiment.

According to one specific embodiment, an array comprises 900 sensor elements (e.g., 30×30), but it should be understood that arrays with fewer (e.g., one or several) or more (e.g., on the order of 10,000 sensor elements (e.g., 100×100)) or more may be implemented. In one aspect, 50 $\mu m^2$ sensor elements with a 50 µm inter-sensor spacing are used. This yields a sensor die that is approximately 30 $mm^2$ for 900 sensor devices (approximately 1 $cm^2$ for 10,000 sensor devices). Devices with arrays preferably operate on a simple row-column addressing scheme with data being multiplexed off chip for A/D conversion and further processing, although other addressing schemes may be used. An example of addressing is shown in FIG. 13. In one aspect, sensors are read serially one at a time. As array sizes increase, more off-chip bandwidth is typically required to ensure latency between sensor readings is minimized. Sensors can then be read out in parallel, for example, a whole row at a time. Other, more advanced schemes for reading out sensors such as "address event" coding may be used. In this method, "important" sensors (i.e., those that are activated) are read out first, and more frequently than other non-activated sensors.

Figure 15:
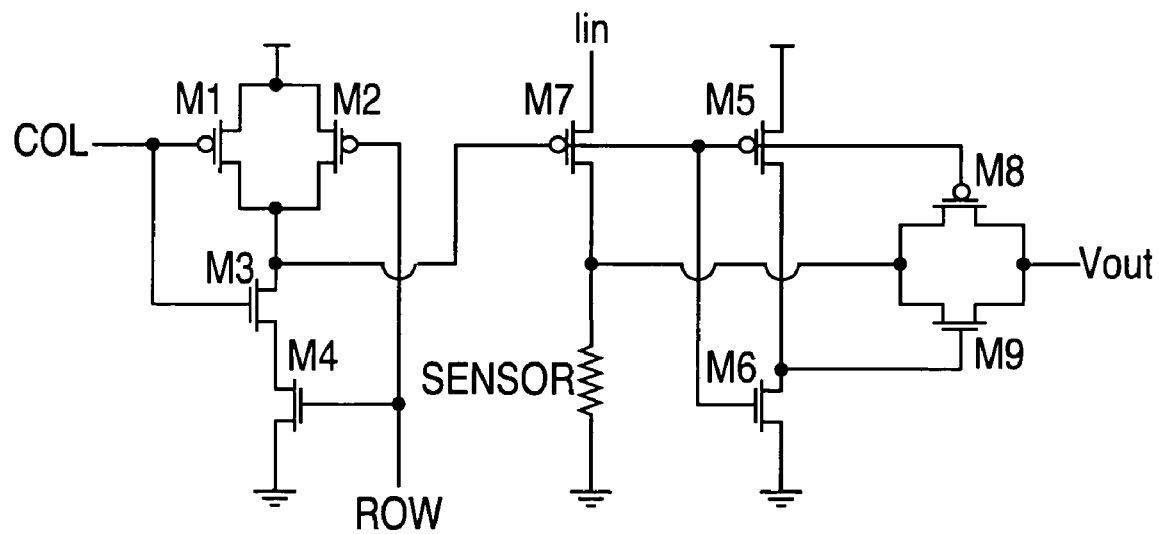
FIG. 15 shows a sensor cell according to one embodiment.

FIG. 15 shows a test unit sensor cell according to one embodiment. The cell as shown is preferably fabricated using a 2 micron CMOS process. The sensor cell includes a switch transistor and decoding logic. In one aspect, transistors at each sensor cell perform decoding, primarliy due to only two metal layers in the IC process. Circuitry M1–M4 decodes X and Y selection signals generated by shift registers on the periphery of the array. The selection signals control a switch (M7) that toggles a current (Iin) through the resistive sensor element. In one aspect of this design, only one sensor is energized at a time to reduce power consumption. To reduce noise and the switch resistance, transistor M7 occupies most of the sensor area. The decoding circuitry also selects a transmission gate (e.g., M5, M6, M8, M9) which passes the sensor voltage to a column output bus. This signal is preferably amplified and transmitted off-chip for processing, although on-chip processing may be performed.

Figure 16:
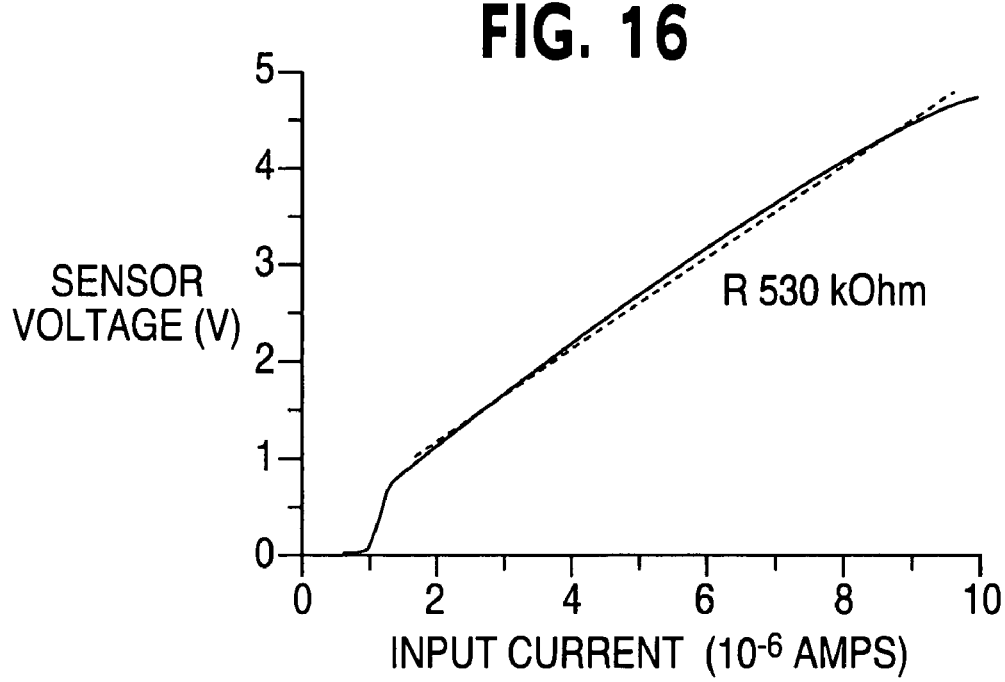
FIG. 16 shows the I-V response of the cell of FIG. 15.
Figure 17:
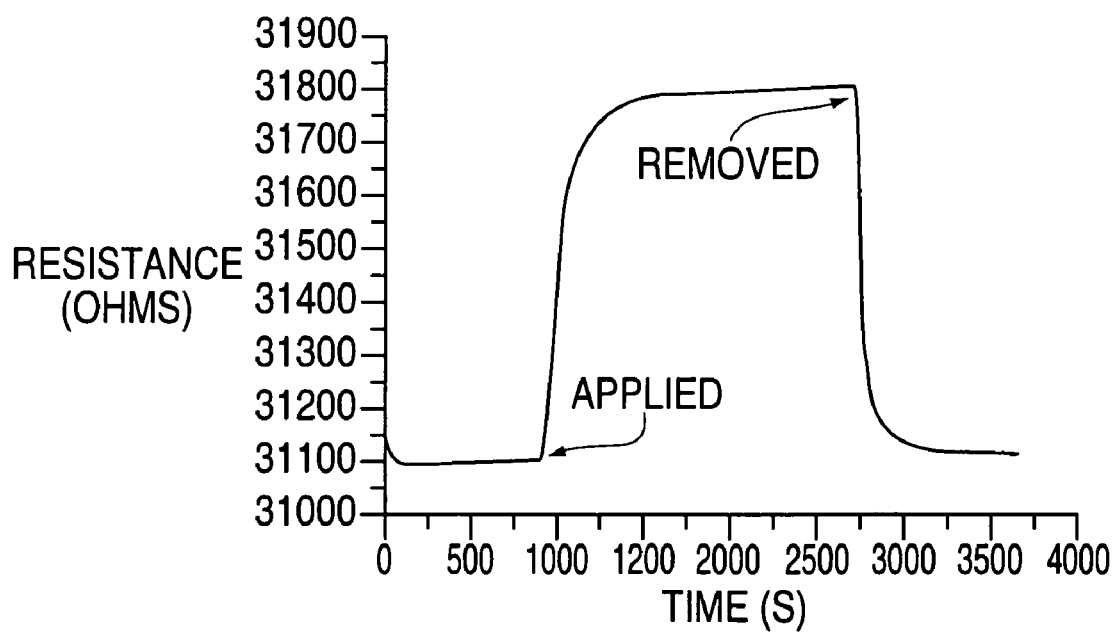
FIG. 17 shows the response of the cell of FIG. 15 to octanol.

FIGS. 16 and 17 show a typical I-V response of such a cell as shown in FIG. 15, and the response of the cell to an exposure of octanol.

Figure 18:
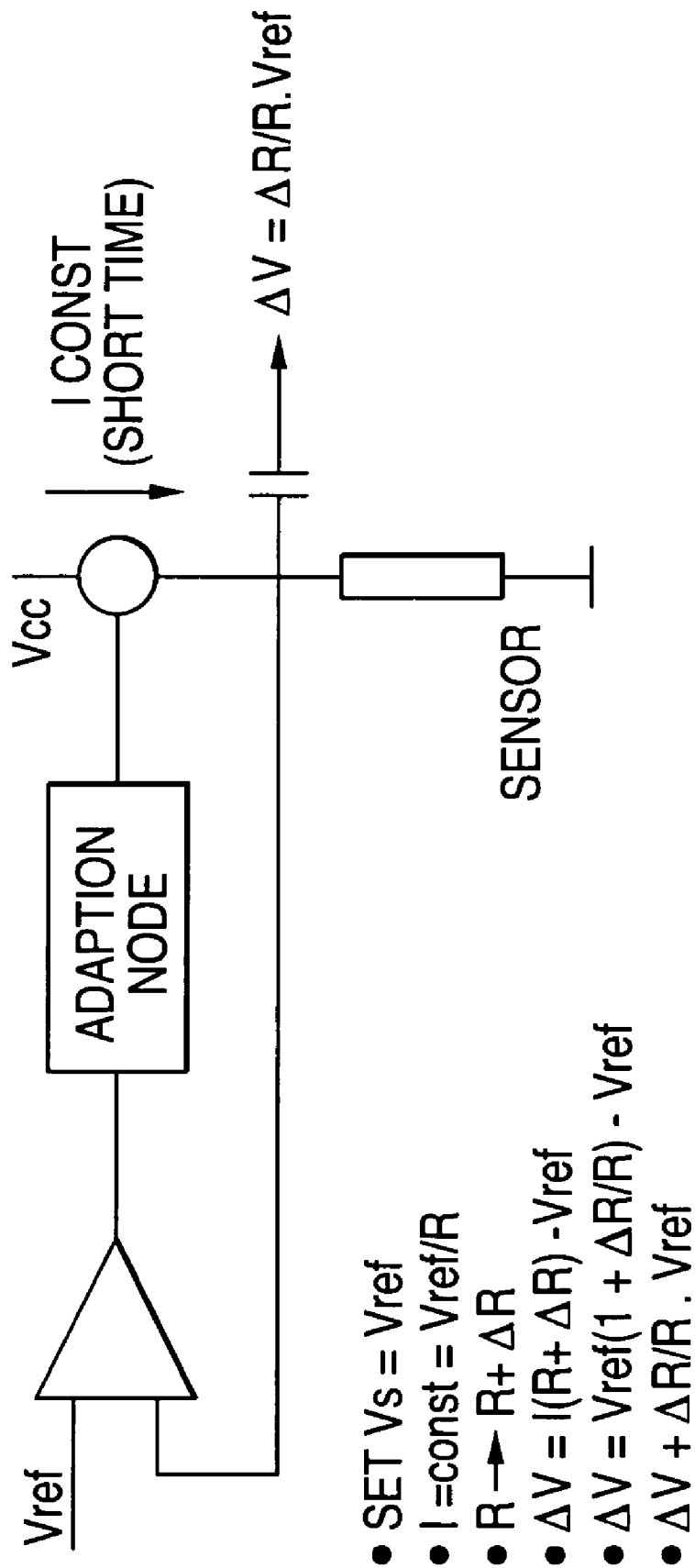
FIG. 18 shows an adaptive bias circuit according to one embodiment.

In one embodiment, analog circuitry is included to provide gain at the sensor, baseline tracking, and ratiometric sensing. Ratiometric sensing enables a direct readout of the key metric $\Delta R/R$, that is, the change in resistance due to the chemical or biologic agent interaction divided by the baseline resistance, without having to calculate this in the microprocessor. FIG. 18 shows an adaptive bias circuit 200 according to one embodiment of the present invention. Circuit 200 provides baseline tracking, ratiometric output and ac coupling in one simple analog circuit.

Although aluminum can be used for conductive traces and leads, it is preferred that an electroless gold procedure is used to produce traces and leads due to the oxidation of aluminum over time. Other conductive may be used.

In one aspect, the present invention provides deposition techniques to efficiently deposit up to thousands of unique sensors in a small area, using for example, ink jetting approaches. Accordingly, the following focuses on useful, jettable formulations, such as formulations of surface-modified carbon black sensors, intrinsically conducting sensors, surface-modified nanoparticle metal sensors, and nanotube based sensors for ink jetting. Once a formulation exists, physical deposition onto a substrate is performed. In one aspect, ink jetting using known ink jet heads is preferably used for deposition. Use of a positioning system that provides x, y and z control of the ink jet head to the micron level is preferred. One such system is provided by Cambridge technologies (formerly Litrex). This system allows for customization of ink jet head and positioning of drops to within 1 micron. This system also provides for layering of drops to build structures such as those required in biogels. The control parameters are determined by the physical characteristics of the formulation, e.g., relationship between drop volume, drying rate (as controlled by substrate temperature and solvent composition), and solids content on deposition consistency as determined by initial resistance.

In certain aspects, a number of surface modified carbon black (SMCB) materials are optimized for chemical and biological sensing. These materials can be produced using a process disclosed in U.S. Pat. No. 6,336,936, and PCT published application WO 01/50117, which are hereby incorporated by reference for all purposes. This process creates a direct chemical attachment of a molecule or polymer to the surface of a carbon black particle. This process results in a highly dispersible particle in the nanometer size regime (e.g., 100 nm is typical), with the chemical differentiation built into the attached organic fragment. It has been demonstrated that these materials have superior sensing properties as compared to chemically similar two-phase (carbon black dispersed in polymer) sensors. In one aspect, this process is used to produce surface modified carbon nanotubes with enhanced dispersion quality In one aspect, four SMCB materials are used which are dispersible in chemically different solvents. These are listed in the table shown in FIG. 19. These materials have been demonstrated to be stable at the nanometer size regime and are excellent ink jetting candidates. Other useful ink-jetting materials and jettable formulations include surface modified gold nanoparticle formulations and nanotube formulations. Such formulations preferably have solid to solvent ratios in the range of about 0.1–5% solids, although greater or lower ratios may be used depending on the formulation, desired ink jetting quality and dispersion stability characteristics.

Solutions and dispersions of intrinsically conducting polymers may also be deposited. Such materials preferably complement the sensing characteristics of the sensors described above. Preferred conductive polymers include polyaniline and polythiophene(s), whose structures are shown in FIGS. 20(a) and (b). During the conversion of these polymers to their conducting state, an anion (or counterion) is formed either as the conjugate acid following protonation of polyaniline, or as an anion of the oxidizing agent in the case of polythiophene. It has been demonstrated that the structure and stoichiometry of these counterions play an important role in the selectivity and sensitivity of the conductive polymer to various VOCs.

Other sensor materials include enzyme-based biogel sensors. Literature reports establish the feasibility of immobilizing enzymes and other proteins in stable, porous, silica glass matrices via an encapsulation process involving sol-gel synthesis methods. For example, as disclosed in U.S. Pat. No. 5,200,334, which is hereby incorporated by reference in its entirety, copper-zinc superoxide dimutase, cytochrome c, and myoglobin can be immobilized using mild conditions such that the biomolecules retain their characteristic reactivities and spectroscopic properties. One key feature in synthesizing this new type of material, termed here as biogel, is the flexible solution chemistry of the sol-gel process. Research in this area has emerged rapidly throughout the world and it is now well established that a wide range of biomolecules retain their characteristic reactivities and chemical function when they are confined within the pores of the sol-gel derived matrix (Avnir et al., *Chem. Mater.*, 6:1605 (1994); Dave et al., *Anal. Chem.*, 66:1120A (1994)). Such an encapsulation process is shown schematically in FIG. 21.

In addition to extending the sol-gel encapsulation process to numerous other enzymes and other proteins, researchers have expanded the types of biomolecular dopants to include antibodies (J. Livage, et al, *J. Sol-Gel Sci. Technol.* 7, 45 (1996)) cells, (E. J. A. Pope, et al, *J. Sol-Gel Sci. Technol.* 8, 635 (1997)), and even photosystems (B. C. Dave, et al, *Mat. Res. Soc. Symp. Proc.* 435,565 (1996)). It is important to emphasize that the biomolecules are physically immobilized and not covalently attached to the inorganic matrix and, therefore, the ability to incorporate biomolecules in the gel requires only that the synthetic conditions do not cause protein aggregation or denaturation (J. M. Miller, et al, *J. Non-Crystalline Solids* 202, 279 (1996)). In general, this means that the sol should have minimal alcohol content and pH near 7. The inclusion of the biomolecule in the starting sol leads to a "templating" effect where the inorganic network grows around the dopant molecule. For this reason, a larger biomolecule is immobilized in the matrix while smaller molecules and ions are free to flow through the porous network. Thus, the microstructure of the sol-gel glass is tailored so that large protein macromolecules are immobilized in the matrix while analytes are free to enter and diffuse through the porous network. Physical entrapment without chemical modification preserves protein structure and functionality and protects the protein from unfolding (denaturation). The unique advantages of sol-gel immobilization include (1) an easy, simple, more universal method as chemical modification is not necessary, (2) increased durability and ruggedness as these materials can be handled without damage to the biomolecules, (3) more flexibility in sensor design as biologically active materials can be prepared as bulk monoliths or as thin films, and (4) increased stability as the biomolecules are physically, chemically, and microbially protected by a glass matrix. This increased stability due to encapsulation in a porous silica glass may be the most important benefit of the sol-gel approach. The thermal stability was also enhanced, as thermal denaturation did not occur in the silica-encapsulated sample until 95° C., whereas denaturation occurred near 65° C. in aqueous buffer. A substantial improvement in the stability of enzymes has also been observed. In studies with butyrylcholinesterase, greater than 80% of enzymatic activity was retained in sol-gel encapsulated samples after 40 days in the absence of preserving agents. In contrast, under the same conditions, enzymatic activity was almost completely lost after about 20 days in aqueous buffer. A remarkable increase in enzyme stability has been reported by Chen, et. al., (Q. Chen, et al, *J. Am. Chem. Soc.* 120, 4582 (1998)) where the half-life of glucose oxidase at 63° C. in a sol-gel silica matrix was 200 times longer than that in aqueous buffer. These results indicate that tremendously enhanced stability of encapsulated bioindicator molecules can be achieved over other reported immobilization techniques, leading to extended device lifetimes. A further advantage of this technique is that liquid nutrient is co-encapsulated with the bioindicator molecule so that the latter can retain its vitality, but the final composition is truly a solid state device and is dry to the touch and the encapsulated materials do not leach from the matrix. Methods to control and modify the pore size have been reported so that analytes that are relatively large can flow through the matrix and interact with the immobilized bioindicator molecule.

Previous reports indicate that sol-gel materials containing physically immobilized bio-molecules can function as the active element or transducer for optical sensing applications. See, e.g., D. Avnir, et al, *Chem. Mater.* 6, 1605 (1994); E. H. Lan, et al, *Mat. Res. Soc. Symp. Proc.* 330, 289 (1994); K. E. Chung, et al, *Anal. Chem.*, 67, 1505 (1995); S. A. Yamanaka, et al, *Chem. Mater.* 4, 495 (1992); S. A. Yamanaka, et al, *J. Sol-Gel Sci. Technol.* 7, 117 (1996); and S. A. Yamanaka, et al, *J. Am. Chem. Soc.* 117, 9095 (1995). In one aspect, devices of the present invention include chemical sensors based on sol-gel glasses doped with enzymes coupled with conductive polymer transducers. These novel materials serve as chemical transducers for a new generation of devices that utilize the molecular recognition processes inherent in biomolecular function and thus provide extraordinary selectivity and sensitivity. Researchers at HRL have recently demonstrated that these sensors respond to aerosolized sporylated bacteria directly without the need for chemical treatments or chemical amplification.

Applications

In addition to the sensor device applications mentioned above, in certain aspects, devices according to the present invention can be used to detect and analyze events and conditions in a wide variety of commercial and non-commercial applications including, but not limited to:

- applications in industries such as utility and power, oil/gas petrochemical, chemical/plastics, automatic ventilation control (cooking, smoking, etc.), heavy industrial manufacturing, environmental toxicology and remediation, biomedicine, cosmetic/perfume, pharmaceutical, transportation, emergency response and law enforcement;
- detection, identification, and/or monitoring of combustible gas, natural gas, $H_2S$, ambient air, emissions control, air intake, smoke, hazardous leak, hazardous spill, fugitive emission, hazardous spill;
- beverage, food, and agricultural products monitoring and control, such as freshness detection, fruit ripening control, fermentation process, and flavor composition and identification;
- detection and identification of illegal substance, explosives, transformer fault, refrigerant and fumigant, formaldehyde, diesel/gasoline/aviation fuel, hospital/medical anesthesia & sterilization gas;

telesurgery, body fluids analysis, drug discovery, infectious disease detection and breath applications, worker protection, arson investigation, personal identification, perimeter monitoring, fragrance formulation; and solvent recovery effectiveness, refueling operations, shipping container inspection, enclosed space surveying, product quality testing, materials quality control, product identification and quality testing.

For example, one recent concern is the intentional release of chemical or biological materials as part of a terrorist activity. While many of the detection attributes are similar between intentional and unintentional release, there may be several key differences. First, the level of leak in an intentional release is likely to be very large, however, the location of the leak is likely to be unknown. Second, the types of materials in the two scenarios are likely to be different (specifically designed chemical or biological agents in the case of an intentional release). The terrorist scenario may require a very large number of very low-cost devices to be deployed at relatively high density in high profile target areas (e.g., public areas such as a stadium, subway, etc.). Sensor devices according to the present invention are very well suited to this application area and will provide a great benefit to homeland security.

Figure 24B:
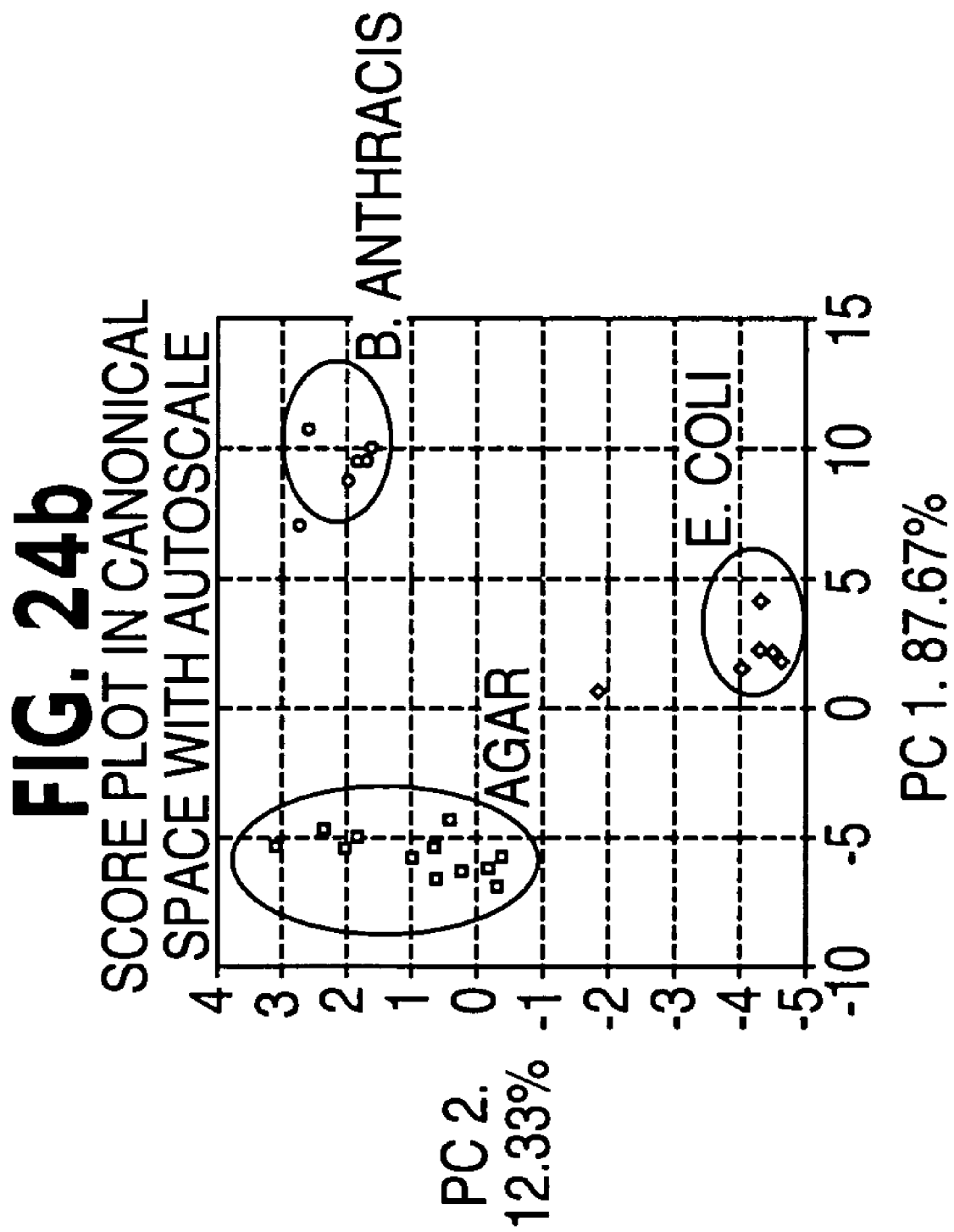
FIG. 24b shows discrimination of bacteria according to one aspect.

Sensor devices and arrays of the present invention are also effective in noninvasive disease diagnostics, for example, by the evaluation of chemical markers in breath or other bodily fluids (e.g., blood and urine). The entire field of metabolomics, correlating biochemical metabolites to disease, is growing in importance. One application is the diagnosis of ventilator associated pneumonia (VAP), a disease that effects many individuals on long term (>48 hour) breathing support. The mortality rate for this disease is high (>25%), owing partly to poor early diagnosis. Low-density (e.g., n=32) chemical sensor arrays have demonstrated a high degree of correlation between breath-based diagnosis and traditional diagnositic measures (composite of temperature, culture, radiography, WBC, RBC) (see FIG. 24). The high density arrays of the present invention would further improve this diagnostic capability and provide for others. Clinical studies are undergoing on a variety of pulmonary disease states with The Cleveland Clinic Foundation including asthma, cystic fibrosis, ARDS (acute respiratory distress syndrome), COPD (chronic obstructive pulmonary disease), and lung cancer. COPD is one of the most common causes of death in the United States, and unlike all other most common killers, the percentage of individuals dying from COPD is actually on the increase (while cancer and heart related deaths are decreasing).

Additional Sensor Types

In certain aspects, devices of the present invention may include many different sensor types in addition to, or in place of, PCS or other chemical sensors. Such additional sensor types include, for example, radiation detection (e.g., geiger, scintillation, solid state), chemical, nuclear, explosive, biological (e.g., DNA, oligonucleotide, antibody-antigen, enzyme reaction, etc) fire detection, and other sensor types. Suitable sensors for the systems and devices of the present invention can also include, but are not limited to, one or more of a conducting/non-conducting region sensor, a SAW sensor, a quartz microbalance sensor, a conductive composite sensor, a chemiresitor, a metal oxide gas sensor, an organic gas sensor, a MOSFET, a piezoelectric device, an infrared sensor, a sintered metal oxide sensor, a Pd-gate MOSFET, a metal FET structure, an electrochemical cell, a conducting polymer sensor, a catalytic gas sensor, an organic semiconducting gas sensor, a solid electrolyte gas sensor, and a piezoelectric quartz crystal sensor. It will be apparent to those of skill in the art that the devices of the present invention can include combinations of one or more of the foregoing sensors and sensor types.

In certain embodiments, an additional sensor can include a single sensor or an array of sensors capable of producing a second response in the presence of physical stimuli. The physical detection sensors detect physical stimuli. Suitable physical stimuli include, but are not limited to, thermal stimuli, radiation stimuli, mechanical stimuli, pressure, visual, magnetic stimuli, and electrical stimuli.

Thermal sensors can detect stimuli which include, but are not limited to, temperature, heat, heat flow, entropy, heat capacity, etc. Radiation sensors can detect stimuli that include, but are not limited to, gamma rays, X-rays, ultraviolet rays, visible, infrared, microwaves and radio waves. Mechanical sensors can detect stimuli which include, but are not limited to, displacement, velocity, acceleration, force, torque, pressure, mass, flow, acoustic wavelength, and amplitude. Magnetic sensors can detect stimuli that include, but are not limited to, magnetic field, flux, magnetic moment, magnetization, and magnetic permeability. Electrical sensors can detect stimuli which include, but are not limited to, charge, current, voltage, resistance, conductance, capacitance, inductance, dielectric permittivity, polarization and frequency.

In certain embodiments, thermal sensors are suitable for use in the present invention. Such thermal sensors include, but are not limited to, thermocouples, such as a semiconducting thermocouples, noise thermometry, thermoswitches, thermistors, metal thermoresistors, semiconducting thermoresistors, thermodiodes, thermotransistors, calorimeters, thermometers, indicators, and fiber optics.

In other embodiments, various radiation sensors are suitable for use in the present invention. Such radiation sensors include, but are not limited to, nuclear radiation microsensors, such as scintillation counters and solid state detectors, ultra-violet, visible and near infrared radiation microsensors, such as photoconductive cells, photodiodes, phototransistors, infrared radiation microsensors, such as photoconductive IR sensors and pyroelectric sensors. Optical sensors also detect visible, near infrared and infrared waves. In certain other embodiments, various mechanical sensors are suitable for use in the present invention and include, but are not limited to, displacement microsensors, capacitive and inductive displacement sensors, optical displacement sensors, ultrasonic displacement sensors, pyroelectric, velocity and flow microsensors, transistor flow microsensors, acceleration microsensors, piezoresistive microaccelerometers, force, pressure and strain microsensors, and piezoelectric crystal sensors.

In certain other embodiments, various chemical or biochemical sensors are suitable for use in the present invention and include, but are not limited to, metal oxide gas sensors, such as tin oxide gas sensors, organic gas sensors, chemocapacitors, chemoidiodes, such as inorganic Schottky device, metal oxide field effect transistor (MOSFET), piezoelectric devices, ion selective FET for pH sensors, polymeric humidity sensors, electrochemical cell sensors, pellistors gas sensors, piezoelectric or surface acoustical wave sensors, infrared sensors, surface plasmon sensors, and fiber optical sensors.

Various other sensors suitable for use in the present invention include, but are not limited to, sintered metal oxide sensors, phthalocyanine sensors, membranes, Pd-gate MOSFET, electrochemical cells, conducting polymer sensors, lipid coating sensors and metal FET structures. In certain preferred embodiments, the sensors include, but are not limited to, metal oxide sensors such as a Tuguchi gas sensors, catalytic gas sensors, organic semiconducting gas sensors, solid electrolyte gas sensors, piezoelectric quartz crystal sensors, fiber optic probes, a micro-electro-mechanical system device, a micro-opto-electro-mechanical system device and Langmuir-Blodgett films.

In another embodiment, the present invention includes detection using sensors as disclosed in U.S. Pat. No. 5,814,524, which issued to Walt, et al., on Sep. 29, 1998, and which is hereby incorporated by reference in its entirety. An optical detection and identification system is disclosed therein that includes an optic sensor, an optic sensing apparatus and methodology for detecting and evaluating one or more analytes of interest, either alone or in mixtures. The system comprises a supporting member and an array formed of heterogeneous, semi-selective polymer films which function as sensing receptor units and are able to detect a variety of different analytes using spectral recognition patterns. Using this system, it is possible to combine viewing and chemical sensing with imaging fiber chemical sensors.

In certain sensor network embodiments, devices of the present invention can include one or more sensors of similar or different type. Also, individual nodes, e.g., individual physical device locations, in a network of nodes can each include one or multiple sensor types. For example, a network may include one person that is wearing a (wireless) device including a single sensor type, a second person that is wearing a (wireless) device including several sensors of the same or different type, a stationary device (wireless or direct connected) that may include one or more sensors of the same or different type, and a network monitor station.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. For example, devices according to the present invention may be used to diagnose diseases using appropriate sensor configurations and analysis algorithms. Therefore, the scope of the appended claims should be accorded the broadest interpretation so as to encompass all such modifications and similar arrangements.

What is claimed is:

1. A biological agent detection apparatus, comprising:
   a substrate;
   an array of two or more sensors arranged on the substrate, wherein at least a first one of the sensors includes a sensing element configured to detect a biological agent;
   a power module for supplying power to the detection apparatus;
   a pick-up antenna, wherein the power is supplied by an external RF field received by the antenna;
   a processing module directly coupled to each of the sensors and configured to process signals received from the two or more sensors to produce an output signal; and
   a communication module configured to provide information to a user in response to the output signal having a value at or above a threshold value,
   wherein the array of two or more sensors includes:
      an activating unit configured to activate only one of said two or more sensors at any point in time, in order to reduce power consumption of the apparatus, wherein the activating unit comprises:
         at least one shift register for selectively accessing one of the two or more sensors;
         decoding circuitry for decoding an output of the at least one shift register;
         a switch for receiving the decoded outputs of the decoding circuitry, and for toggling a current based on the decoded outputs; and
         a resistive sensor element for receiving the toggled current, wherein the toggled current is utilized to access only one of the two or more sensors at any point in time.

2. The apparatus of claim 1, wherein the processor is configured to execute a first process that detects a change in an environmental condition, and a second process that identifies an origin of the change in the environmental condition.

3. The apparatus of claim 2, wherein the second process includes a pattern recognition algorithm.

4. The apparatus of claim 1, further including a communication module configured to provide the output signal to an external intelligence device.

5. The apparatus of claim 4, wherein the communication module includes one of a wireless interface and a physical bus interface for communicating with the external intelligence device.

6. The apparatus of claim 5, wherein the wireless interface device includes one of an RF transmitter, an RF transceiver, an IR transmitter and an IR transceiver.

7. The apparatus of claim 5, wherein the physical bus interface includes one of an RS-232 port, a USB port and a Firewire port.

8. The apparatus of claim 1, wherein the communication module includes one of a LED, speaker, buzzer and vibration mechanism.

9. The apparatus of claim 1, wherein at least two of the sensors are polymer composite sensors.

10. The apparatus of claim 1, wherein at least a second one of the sensors is a chemical sensor.

11. The apparatus of claim 1, wherein the sensing element of the first sensor is selected from the group consisting of a polymer composite sensor, a surface modified carbon black sensor, a sol-gel encapsulated enzyme, a biopolymer, a self assembling monolayer, an intrinsically conducting polymer, a carbon nanotube composite, a nanogold composite and a nanoscale polymer composite.

12. The apparatus of claim 1, wherein the apparatus has a dimension of less than about 4 square inches.

13. The apparatus of claim 1, wherein the apparatus has a dimension of less than about 1 square inch.

14. The apparatus of claim 1, wherein the sensors and the processing module are integrated on the substrate.

15. The apparatus of claim 1, further including an attachment mechanism for allowing a user to wear the apparatus.

16. The apparatus of claim 15, wherein the attachment mechanism includes one of a clip and a pin.

17. The apparatus of claim 1, wherein the sensing element of the first sensor is an intrinsically conducting polymer selected from the group consisting of polyaniline and polythiophene.

18. The apparatus of claim 1, wherein the apparatus is used to diagnose a disease or determine a biological agent based on sampling the atmosphere or a bodily fluid.

19. The apparatus of claim 1, wherein a second one of the sensors includes a sensing element configured to detect a biological element different from the biological agent detectable by the first sensor.

20. The apparatus of claim 19, further comprising a communication module configured to communicate with an external processor.

21. The apparatus of claim 20, wherein the communication module includes a wireless transmitter device.

22. The apparatus of claim 21, wherein the wireless transmitter device includes one of an RF transmitter and an IR transmitter.

23. The apparatus of claim 1, further comprising a transistor housed on the substrate and configured to reduce noise and switch resistance for the two or more sensors.

24. The apparatus of claim 1, further comprising analog circuitry configured to provide gain, baseline tracking and radiometric sensing.

25. The apparatus of claim 1, further comprising:
wakeup circuitry coupled to the power module and configured to activate the two or more sensors at periodic intervals, and to turn off the two of more sensors at all other times between adjacent ones of the periodic intervals.

26. The apparatus of claim 25, wherein the apparatus is maintained in a lower-power-consumption ON mode during the all other times between the adjacent ones of the periodic intervals.

27. A biological agent detection apparatus, comprising:
a substrate;
an array of two or more sensors arranged on the substrate, wherein at least a first one of the sensors includes a sensing element configured to detect a biological agent;
a power module for supplying power to the detection apparatus;
a pick-up antenna, wherein the power is supplied by an external RF field received by the antenna;
a processing module directly coupled to each of the sensors and configured to process signals received from the two or more sensors to produce an output signal;
a communication module configured to provide information to a user in response to the output signal having a value at or above a threshold value; and
a controlling unit configured to control the processing module to cause the processing module to read out the signals from the two or more sensors in a particular sequential order, so as to prioritize certain sensors of the two or more sensors with respect to other sensors of the two or more sensors,
wherein the array of two or more sensors includes:
an activating unit configured to activate only one of said two or more sensors at any point in time, in order to reduce power consumption of the apparatus.

* * * * *